(12) United States Patent
Casey

(10) Patent No.: US 11,517,340 B2
(45) Date of Patent: Dec. 6, 2022

(54) STENTRIEVER DEVICES FOR REMOVING AN OCCLUSIVE CLOT FROM A VESSEL AND METHODS THEREOF

(71) Applicant: NEURAVI LIMITED, Galway (IE)

(72) Inventor: Brendan Casey, Galway (IE)

(73) Assignee: NEURAVI LIMITED, Galway (IE)

( * ) Notice: Subject to any disclaimer, the term of this patent is extended or adjusted under 35 U.S.C. 154(b) by 69 days.

(21) Appl. No.: 16/701,323

(22) Filed: Dec. 3, 2019

(65) Prior Publication Data

US 2021/0161544 A1 Jun. 3, 2021

(51) Int. Cl.
*A61B 17/221* (2006.01)
*A61B 17/22* (2006.01)
*A61B 17/00* (2006.01)

(52) U.S. Cl.
CPC .. *A61B 17/221* (2013.01); *A61B 2017/00867* (2013.01); *A61B 2017/2215* (2013.01); *A61B 2017/22079* (2013.01)

(58) Field of Classification Search
CPC ........ A61B 17/221; A61B 2017/00867; A61B 2017/22079; A61B 2017/2215
USPC ........................................................ 606/200
See application file for complete search history.

(56) References Cited

U.S. PATENT DOCUMENTS

| | | |
|---|---|---|
| 4,455,717 A | 6/1984 | Gray |
| 4,611,594 A | 9/1986 | Grayhack et al. |
| 4,612,931 A | 9/1986 | Dormia |
| 4,727,873 A | 3/1988 | Mobin-Uddin |
| 4,793,348 A | 12/1988 | Palmaz |
| 4,873,978 A | 10/1989 | Ginsburg |
| 5,011,488 A | 4/1991 | Ginsburg |
| 5,084,065 A | 1/1992 | David et al. |
| 5,092,839 A | 3/1992 | Kipperman |
| 5,100,423 A | 3/1992 | Fearnot |
| 5,102,415 A | 4/1992 | Guenther et al. |
| 5,108,419 A | 4/1992 | Reger et al. |

(Continued)

FOREIGN PATENT DOCUMENTS

| | | |
|---|---|---|
| CN | 2557083 Y | 6/2003 |
| CN | 101172051 A | 5/2008 |

(Continued)

OTHER PUBLICATIONS

US 6,348,062 B1, 02/2002, Hopkins et al. (withdrawn)

*Primary Examiner* — Kathleen S Holwerda
*Assistant Examiner* — Kankindi Rwego
(74) *Attorney, Agent, or Firm* — Troutman Pepper Hamilton Sanders LLP

(57) ABSTRACT

Devices described herein include a stentriever for removing an occlusive clot. The stentriever can include a membrane cover on the proximal end which can be sized to form a seal with the tip of an intermediate catheter. Clot engagement sections and/or a distal engagement section of the stentriever can also include a full or partial membrane covering to control the direction of aspiration and/or areas where the aspiration applies suction to the thrombus or clot. The membranes can be used to direct the aspiration so as to pull the clot deeper into the clot engagement sections of the stentriever, thereby improving grip on the clot. The design can also increase the effectiveness of clot fragment protection for friable clots by providing pores and/or clot cells in a distal engagement section.

14 Claims, 8 Drawing Sheets

(56) References Cited

U.S. PATENT DOCUMENTS

| | | | |
|---|---|---|---|
| 5,122,136 A | 6/1992 | Guglielmi et al. | |
| 5,163,951 A | 11/1992 | Pinchuk et al. | |
| 5,171,233 A | 12/1992 | Amplatz et al. | |
| 5,171,259 A | 12/1992 | Inoue | |
| 5,217,441 A | 6/1993 | Shichman | |
| 5,234,437 A | 8/1993 | Sepetka | |
| 5,236,447 A | 8/1993 | Kubo et al. | |
| 5,330,482 A | 7/1994 | Gibbs et al. | |
| 5,383,887 A | 1/1995 | Nadal | |
| 5,387,219 A | 2/1995 | Rappe | |
| 5,387,226 A | 2/1995 | Miraki | |
| 5,449,372 A | 9/1995 | Schmaltz et al. | |
| 5,499,985 A | 3/1996 | Hein et al. | |
| 5,538,512 A | 7/1996 | Zenzon et al. | |
| 5,538,515 A | 7/1996 | Kafry et al. | |
| 5,549,626 A | 8/1996 | Miller et al. | |
| 5,558,652 A | 9/1996 | Henke | |
| 5,609,627 A | 3/1997 | Goicoechea et al. | |
| 5,624,461 A | 4/1997 | Mariant | |
| 5,639,277 A | 6/1997 | Mariant et al. | |
| 5,639,278 A | 6/1997 | Dereume et al. | |
| 5,645,558 A | 7/1997 | Horton | |
| 5,653,605 A | 8/1997 | Woehl et al. | |
| 5,658,296 A | 8/1997 | Bates et al. | |
| 5,665,117 A | 9/1997 | Rhodes | |
| 5,695,519 A | 12/1997 | Summers et al. | |
| 5,709,704 A | 1/1998 | Nott et al. | |
| 5,713,853 A | 2/1998 | Clark et al. | |
| 5,769,871 A | 6/1998 | Mers Kelly et al. | |
| 5,769,884 A | 6/1998 | Solovay | |
| 5,779,686 A | 7/1998 | Sato et al. | |
| 5,779,716 A | 7/1998 | Cano et al. | |
| 5,800,519 A | 9/1998 | Sandock | |
| 5,810,874 A | 9/1998 | Lefebvre | |
| 5,814,064 A * | 9/1998 | Daniel | A61F 2/0108 606/159 |
| 5,827,304 A | 10/1998 | Hart | |
| 5,853,422 A | 12/1998 | Huebsch et al. | |
| 5,855,598 A | 1/1999 | Pinchuk | |
| 5,893,869 A | 4/1999 | Barnhart et al. | |
| 5,895,398 A | 4/1999 | Wensel et al. | |
| 5,897,567 A | 4/1999 | Ressemann et al. | |
| 5,904,698 A | 5/1999 | Thomas et al. | |
| 5,911,702 A | 6/1999 | Romley et al. | |
| 5,911,725 A | 6/1999 | Boury | |
| 5,919,126 A | 7/1999 | Armini | |
| 5,931,509 A | 8/1999 | Bartholomew | |
| 5,935,139 A | 8/1999 | Bates | |
| 5,947,995 A | 9/1999 | Samuels | |
| 6,063,113 A | 5/2000 | Kavteladze et al. | |
| 6,066,149 A | 5/2000 | Samson et al. | |
| 6,066,158 A | 5/2000 | Engelson et al. | |
| 6,093,196 A | 7/2000 | Okada | |
| 6,093,199 A | 7/2000 | Brown et al. | |
| 6,096,053 A | 8/2000 | Bates | |
| 6,099,534 A | 8/2000 | Bates et al. | |
| 6,099,559 A | 8/2000 | Nolting | |
| 6,102,932 A | 8/2000 | Kurz | |
| 6,106,548 A | 8/2000 | Roubin et al. | |
| 6,129,739 A | 10/2000 | Khosravi | |
| 6,143,022 A | 11/2000 | Shull et al. | |
| 6,146,404 A | 11/2000 | Kim et al. | |
| 6,156,064 A | 12/2000 | Chouinard | |
| 6,165,194 A | 12/2000 | Denardo | |
| 6,165,199 A | 12/2000 | Barbut | |
| 6,168,604 B1 | 1/2001 | Cano | |
| 6,168,622 B1 | 1/2001 | Mazzocchi | |
| 6,174,318 B1 | 1/2001 | Bates et al. | |
| 6,179,861 B1 | 1/2001 | Khosravi et al. | |
| 6,203,561 B1 | 3/2001 | Ramee et al. | |
| 6,214,026 B1 | 4/2001 | Lepak et al. | |
| 6,221,006 B1 | 4/2001 | Dubrul et al. | |
| 6,221,096 B1 | 4/2001 | Aiba et al. | |
| 6,231,597 B1 | 5/2001 | Deem et al. | |
| 6,238,412 B1 | 5/2001 | Dubrul et al. | |
| 6,245,012 B1 | 6/2001 | Kleshinski | |
| 6,245,087 B1 | 6/2001 | Addis | |
| 6,251,122 B1 | 6/2001 | Tsukernik | |
| 6,254,571 B1 | 7/2001 | Hart | |
| 6,264,663 B1 | 7/2001 | Cano | |
| 6,267,777 B1 | 7/2001 | Bosma et al. | |
| 6,290,710 B1 | 9/2001 | Cryer et al. | |
| 6,312,444 B1 | 11/2001 | Barbut | |
| 6,315,778 B1 | 11/2001 | Gambale et al. | |
| 6,325,815 B1 | 12/2001 | Kusleika et al. | |
| 6,325,819 B1 | 12/2001 | Pavcnik et al. | |
| 6,334,864 B1 | 1/2002 | Amplatz et al. | |
| 6,336,934 B1 | 1/2002 | Gilson et al. | |
| 6,346,116 B1 | 2/2002 | Brooks et al. | |
| 6,348,056 B1 | 2/2002 | Bates et al. | |
| 6,350,271 B1 | 2/2002 | Kurz et al. | |
| 6,355,057 B1 | 3/2002 | DeMarais et al. | |
| 6,361,545 B1 | 3/2002 | Macoviak et al. | |
| 6,364,895 B1 | 4/2002 | Greenhalgh | |
| 6,375,668 B1 | 4/2002 | Gifford et al. | |
| 6,375,670 B1 | 4/2002 | Greenhalgh | |
| 6,383,205 B1 | 5/2002 | Samson et al. | |
| 6,383,206 B1 | 5/2002 | Gillick et al. | |
| 6,391,037 B1 | 5/2002 | Greenhalgh | |
| 6,402,771 B1 | 6/2002 | Palmer et al. | |
| 6,416,541 B2 | 7/2002 | Denardo | |
| 6,425,909 B1 | 7/2002 | Dieck et al. | |
| 6,428,558 B1 | 8/2002 | Jones et al. | |
| 6,432,122 B1 | 8/2002 | Gilson et al. | |
| 6,436,112 B2 | 8/2002 | Wensel et al. | |
| 6,458,139 B1 | 10/2002 | Palmer et al. | |
| 6,485,497 B2 | 11/2002 | Wensel et al. | |
| 6,485,501 B1 | 11/2002 | Green | |
| 6,485,502 B2 | 11/2002 | Don Michael et al. | |
| 6,488,701 B1 | 12/2002 | Nolting et al. | |
| 6,511,492 B1 | 1/2003 | Rosenbluth et al. | |
| 6,530,935 B2 | 3/2003 | Wensel et al. | |
| 6,530,939 B1 | 3/2003 | Hopkins et al. | |
| 6,540,768 B1 | 4/2003 | Diaz et al. | |
| 6,544,279 B1 | 4/2003 | Hopkins et al. | |
| 6,551,341 B2 | 4/2003 | Boylan et al. | |
| 6,551,342 B1 | 4/2003 | Shen et al. | |
| 6,575,996 B1 | 6/2003 | Denison et al. | |
| 6,575,997 B1 | 6/2003 | Palmer et al. | |
| 6,582,448 B1 | 6/2003 | Boyle et al. | |
| 6,585,756 B1 | 7/2003 | Strecker | |
| 6,589,265 B1 | 7/2003 | Palmer et al. | |
| 6,592,607 B1 | 7/2003 | Palmer et al. | |
| 6,592,614 B2 | 7/2003 | Lenker et al. | |
| 6,592,616 B1 | 7/2003 | Stack et al. | |
| 6,602,265 B2 | 8/2003 | Dubrul et al. | |
| 6,602,271 B2 | 8/2003 | Adams et al. | |
| 6,602,272 B2 | 8/2003 | Boylan et al. | |
| 6,605,102 B1 | 8/2003 | Mazzocchi et al. | |
| 6,610,077 B1 | 8/2003 | Hancock et al. | |
| 6,616,679 B1 | 9/2003 | Khosravi et al. | |
| 6,632,241 B1 | 10/2003 | Hancock et al. | |
| 6,638,245 B2 | 10/2003 | Miller et al. | |
| 6,638,293 B1 | 10/2003 | Makower et al. | |
| 6,641,590 B1 | 11/2003 | Palmer et al. | |
| 6,656,218 B1 | 12/2003 | Denardo et al. | |
| 6,660,021 B1 | 12/2003 | Palmer et al. | |
| 6,663,650 B2 | 12/2003 | Sepetka et al. | |
| 6,673,089 B1 | 1/2004 | Yassour et al. | |
| 6,685,722 B1 | 2/2004 | Rosenbluth et al. | |
| 6,692,504 B2 | 2/2004 | Kurz et al. | |
| 6,692,508 B2 | 2/2004 | Wensel et al. | |
| 6,692,509 B2 | 2/2004 | Wensel et al. | |
| 6,695,858 B1 | 2/2004 | Dubrul et al. | |
| 6,702,782 B2 | 3/2004 | Miller et al. | |
| 6,709,465 B2 | 3/2004 | Mitchell et al. | |
| 6,712,834 B2 | 3/2004 | Yassour et al. | |
| 6,726,701 B2 | 4/2004 | Gilson et al. | |
| 6,726,703 B2 | 4/2004 | Broome et al. | |
| 6,730,104 B1 | 5/2004 | Sepetka et al. | |
| 6,783,528 B2 | 8/2004 | Vincent-Prestigiacomo | |
| 6,783,538 B2 | 8/2004 | McGuckin, Jr. et al. | |
| 6,824,545 B2 | 11/2004 | Sepetka et al. | |
| 6,855,155 B2 | 2/2005 | Denardo et al. | |

(56) References Cited

U.S. PATENT DOCUMENTS

| | | |
|---|---|---|
| 6,878,163 B2 | 4/2005 | Denardo et al. |
| 6,890,340 B2 | 5/2005 | Duane |
| 6,913,612 B2 | 7/2005 | Palmer et al. |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi et al. |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,008,434 B2 | 3/2006 | Kurz et al. |
| 7,033,376 B2 | 4/2006 | Tsukernik |
| 7,041,116 B2 | 5/2006 | Goto et al. |
| 7,048,758 B2 | 5/2006 | Boyle et al. |
| 7,052,500 B2 | 5/2006 | Bashiri et al. |
| 7,058,456 B2 | 6/2006 | Pierce |
| 7,063,707 B2 | 6/2006 | Bose et al. |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Molaei |
| 7,179,273 B1 | 2/2007 | Palmer et al. |
| 7,185,922 B2 | 3/2007 | Takayanagi et al. |
| 7,220,271 B2 | 5/2007 | Clubb et al. |
| 7,226,464 B2 | 6/2007 | Garner et al. |
| 7,229,472 B2 | 6/2007 | DePalma et al. |
| 7,241,304 B2 | 7/2007 | Boyle et al. |
| 7,288,112 B2 | 10/2007 | Denardo et al. |
| 7,300,458 B2 | 11/2007 | Henkes et al. |
| 7,306,618 B2 | 12/2007 | Demond et al. |
| 7,314,483 B2 | 1/2008 | Landau et al. |
| 7,316,692 B2 | 1/2008 | Huffmaster |
| 7,323,001 B2 | 1/2008 | Clubb et al. |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins et al. |
| 7,425,215 B2 | 9/2008 | Boyle et al. |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka et al. |
| 7,556,636 B2 | 7/2009 | Mazzocchi et al. |
| 7,582,111 B2 | 9/2009 | Krolik et al. |
| 7,594,926 B2 | 9/2009 | Linder et al. |
| 7,604,649 B2 | 10/2009 | McGuckin, Jr. et al. |
| 7,604,650 B2 | 10/2009 | Bergheim |
| 7,618,434 B2 | 11/2009 | Santra et al. |
| 7,662,165 B2 | 2/2010 | Gilson et al. |
| 7,670,356 B2 | 3/2010 | Mazzocchi et al. |
| 7,678,123 B2 | 3/2010 | Chanduszko |
| 7,691,121 B2 | 4/2010 | Rosenbluth et al. |
| 7,691,124 B2 | 4/2010 | Balgobin |
| 7,708,770 B2 | 5/2010 | Linder et al. |
| 7,717,929 B2 | 5/2010 | Fallman |
| 7,736,385 B2 | 6/2010 | Agnew |
| 7,758,606 B2 | 7/2010 | Streeter et al. |
| 7,758,611 B2 | 7/2010 | Kato |
| 7,766,934 B2 | 8/2010 | Pal et al. |
| 7,771,452 B2 | 8/2010 | Pal et al. |
| 7,780,694 B2 | 8/2010 | Palmer et al. |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi et al. |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,175 B2 | 12/2010 | Bonnette et al. |
| 7,846,176 B2 | 12/2010 | Gilson et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | OBrien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Garrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,282,668 B2 | 10/2012 | McGuckin, Jr. et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III et al. |
| 8,357,893 B2 | 1/2013 | Xu et al. |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |

(56) References Cited

U.S. PATENT DOCUMENTS

| | | |
|---|---|---|
| 8,900,265 B1 | 12/2014 | Ulm, III |
| 8,920,358 B2 | 12/2014 | Levine et al. |
| 8,939,991 B2 | 1/2015 | Krolik et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,211,132 B2 | 12/2015 | Bowman |
| 9,232,992 B2 | 1/2016 | Heidner |
| 9,254,371 B2 | 2/2016 | Martin et al. |
| 9,301,769 B2 | 4/2016 | Brady et al. |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Peterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,304 B2 | 12/2017 | Horan et al. |
| 9,833,604 B2 | 12/2017 | Lam |
| 9,833,625 B2 | 12/2017 | Waldhauser et al. |
| 9,901,434 B2 | 2/2018 | Hoffman |
| 9,918,720 B2 | 3/2018 | Marchand et al. |
| 10,016,206 B1 | 7/2018 | Yang |
| 10,070,878 B2 | 9/2018 | Ma |
| 10,098,651 B2 | 10/2018 | Marchand et al. |
| 10,201,360 B2 | 2/2019 | Vale et al. |
| 10,231,751 B2 | 3/2019 | Sos |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,524,811 B2 | 1/2020 | Marchand et al. |
| 10,617,435 B2 | 4/2020 | Vale et al. |
| 10,722,257 B2 | 7/2020 | Skillrud et al. |
| 2001/0001315 A1 | 5/2001 | Bates et al. |
| 2001/0016755 A1 | 8/2001 | Addis |
| 2001/0037141 A1 | 11/2001 | Yee et al. |
| 2001/0041909 A1 | 11/2001 | Tsugita et al. |
| 2001/0049554 A1 | 12/2001 | Ruiz et al. |
| 2001/0051810 A1 | 12/2001 | Dubrul et al. |
| 2002/0004667 A1 | 1/2002 | Adams et al. |
| 2002/0016609 A1 | 2/2002 | Wensel et al. |
| 2002/0022859 A1 | 2/2002 | Hogendijk |
| 2002/0026211 A1 | 2/2002 | Khosravi et al. |
| 2002/0042627 A1 | 4/2002 | Brady et al. |
| 2002/0049468 A1 | 4/2002 | Streeter et al. |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka et al. |
| 2002/0082558 A1 | 6/2002 | Samson et al. |
| 2002/0091407 A1 | 7/2002 | Zadno-Azizi et al. |
| 2002/0095171 A1 | 7/2002 | Belef |
| 2002/0123765 A1 | 9/2002 | Sepetka et al. |
| 2002/0138094 A1 | 9/2002 | Borillo et al. |
| 2002/0143349 A1 | 10/2002 | Gifford, III et al. |
| 2002/0143362 A1 | 10/2002 | Macoviak et al. |
| 2002/0156455 A1 | 10/2002 | Barbut |
| 2002/0161393 A1 | 10/2002 | Demond et al. |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans et al. |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest et al. |
| 2003/0004540 A1 | 1/2003 | Linder et al. |
| 2003/0004542 A1 | 1/2003 | Wensel et al. |
| 2003/0009146 A1 | 1/2003 | Muni et al. |
| 2003/0009191 A1 | 1/2003 | Wensel et al. |
| 2003/0038447 A1 | 2/2003 | Cantele |
| 2003/0040772 A1 | 2/2003 | Hyodoh et al. |
| 2003/0050663 A1 | 3/2003 | Khachin et al. |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady et al. |
| 2003/0153943 A1 | 8/2003 | Michael et al. |
| 2003/0153944 A1 | 8/2003 | Phung et al. |
| 2003/0163064 A1 | 8/2003 | Vrba et al. |
| 2003/0163158 A1 | 8/2003 | White |
| 2003/0171769 A1 | 9/2003 | Barbut |
| 2003/0171771 A1 | 9/2003 | Anderson et al. |

(56) References Cited

U.S. PATENT DOCUMENTS

| | | |
|---|---|---|
| 2003/0176884 A1 | 9/2003 | Berrada et al. |
| 2003/0187495 A1 | 10/2003 | Cully et al. |
| 2003/0195537 A1 | 10/2003 | Dubrul et al. |
| 2003/0195554 A1 | 10/2003 | Shen et al. |
| 2003/0199917 A1 | 10/2003 | Knudson et al. |
| 2003/0204202 A1 | 10/2003 | Palmer et al. |
| 2003/0208224 A1 | 11/2003 | Broome |
| 2003/0212430 A1 | 11/2003 | Bose et al. |
| 2003/0236533 A1 | 12/2003 | Wilson et al. |
| 2004/0064179 A1 | 4/2004 | Linder et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0082962 A1 | 4/2004 | Demarais et al. |
| 2004/0082967 A1 | 4/2004 | Broome et al. |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland et al. |
| 2004/0133232 A1 | 7/2004 | Rosenbluth et al. |
| 2004/0138692 A1 | 7/2004 | Phung et al. |
| 2004/0153117 A1 | 8/2004 | Clubb et al. |
| 2004/0153118 A1 | 8/2004 | Clubb et al. |
| 2004/0199201 A1 | 10/2004 | Kellett et al. |
| 2004/0215318 A1 | 10/2004 | Kwitkin |
| 2004/0220663 A1 | 11/2004 | Rivelli |
| 2005/0033348 A1 | 2/2005 | Sepetka et al. |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka et al. |
| 2005/0049669 A1 | 3/2005 | Jones et al. |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka et al. |
| 2005/0085849 A1 | 4/2005 | Sepetka et al. |
| 2005/0090779 A1 | 4/2005 | Osypka |
| 2005/0090857 A1 | 4/2005 | Kusleika et al. |
| 2005/0125024 A1 | 6/2005 | Sepetka et al. |
| 2005/0171566 A1 | 8/2005 | Kanamaru |
| 2005/0192627 A1 | 9/2005 | Whisenant et al. |
| 2005/0216030 A1 | 9/2005 | Sepetka et al. |
| 2005/0216050 A1 | 9/2005 | Sepetka et al. |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka et al. |
| 2006/0009798 A1 | 1/2006 | Callister et al. |
| 2006/0009799 A1 | 1/2006 | Kleshinski et al. |
| 2006/0020285 A1 | 1/2006 | Niermann |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0064151 A1 | 3/2006 | Guterman |
| 2006/0069424 A1 | 3/2006 | Acosta et al. |
| 2006/0074477 A1 | 4/2006 | Berthiaume et al. |
| 2006/0149313 A1 | 7/2006 | Arguello et al. |
| 2006/0155305 A1 | 7/2006 | Freudenthal et al. |
| 2006/0161187 A1 | 7/2006 | Levine et al. |
| 2006/0195137 A1 | 8/2006 | Sepetka et al. |
| 2006/0224177 A1 | 10/2006 | Finitsis |
| 2006/0224179 A1 | 10/2006 | Kucharczyk et al. |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1 | 4/2007 | Pal et al. |
| 2007/0100348 A1 | 5/2007 | Cauthen, III et al. |
| 2007/0118173 A1 | 5/2007 | Magnuson et al. |
| 2007/0149997 A1 | 6/2007 | Muller |
| 2007/0156170 A1 | 7/2007 | Hancock et al. |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslavski et al. |
| 2007/0198051 A1 | 8/2007 | Clubb et al. |
| 2007/0198075 A1 | 8/2007 | Levy |
| 2007/0208367 A1 | 9/2007 | Fiorella et al. |
| 2007/0208371 A1 | 9/2007 | French et al. |
| 2007/0225749 A1 | 9/2007 | Martin et al. |
| 2007/0233175 A1 | 10/2007 | Zaver et al. |
| 2007/0244505 A1 | 10/2007 | Gilson et al. |
| 2007/0270902 A1 | 11/2007 | Slazas et al. |
| 2007/0288054 A1 | 12/2007 | Tanaka et al. |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney et al. |
| 2008/0097386 A1 | 4/2008 | Osypka |
| 2008/0109031 A1 | 5/2008 | Sepetka et al. |
| 2008/0109032 A1 | 5/2008 | Sepetka et al. |
| 2008/0119886 A1 | 5/2008 | Greenhalgh et al. |
| 2008/0125798 A1 | 5/2008 | Osborne et al. |
| 2008/0177296 A1 | 7/2008 | Sepetka et al. |
| 2008/0178890 A1 | 7/2008 | Townsend et al. |
| 2008/0183197 A1 | 7/2008 | Sepetka et al. |
| 2008/0183198 A1 | 7/2008 | Sepetka et al. |
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0188887 A1 | 8/2008 | Batiste |
| 2008/0200946 A1 | 8/2008 | Braun et al. |
| 2008/0200947 A1 | 8/2008 | Kusleika et al. |
| 2008/0215077 A1 | 9/2008 | Sepetka et al. |
| 2008/0221600 A1 | 9/2008 | Dieck et al. |
| 2008/0228209 A1 | 9/2008 | DeMello et al. |
| 2008/0234706 A1 | 9/2008 | Sepetka et al. |
| 2008/0243170 A1 | 10/2008 | Jenson et al. |
| 2008/0255596 A1 | 10/2008 | Jenson et al. |
| 2008/0262410 A1 | 10/2008 | Jenson et al. |
| 2008/0262528 A1 | 10/2008 | Martin |
| 2008/0262532 A1 | 10/2008 | Martin |
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel et al. |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin et al. |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0292297 A1 | 11/2009 | Ferrere |
| 2009/0292307 A1 | 11/2009 | Razack |
| 2009/0299393 A1 | 12/2009 | Martin et al. |
| 2009/0299403 A1 | 12/2009 | Chanduszko et al. |
| 2009/0306702 A1 | 12/2009 | Miloslavski et al. |
| 2009/0326636 A1 | 12/2009 | Hashimoto et al. |

(56) References Cited

U.S. PATENT DOCUMENTS

| | | |
|---|---|---|
| 2010/0004607 A1 | 1/2010 | Wilson et al. |
| 2010/0076482 A1 | 3/2010 | Shu et al. |
| 2010/0087850 A1* | 4/2010 | Razack ............ A61B 17/32075 |
| | | 606/200 |
| 2010/0087908 A1 | 4/2010 | Hilaire et al. |
| 2010/0114017 A1 | 5/2010 | Lenker et al. |
| 2010/0125326 A1 | 5/2010 | Kalstad et al. |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnette et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009950 A1 | 1/2011 | Grandfield et al. |
| 2011/0015718 A1 | 1/2011 | Schreck |
| 2011/0022149 A1 | 1/2011 | Cox et al. |
| 2011/0040319 A1 | 2/2011 | Fulton, III |
| 2011/0054504 A1 | 3/2011 | Porter |
| 2011/0054514 A1 | 3/2011 | Arcand et al. |
| 2011/0054516 A1 | 3/2011 | Keegan et al. |
| 2011/0060212 A1 | 3/2011 | Slee et al. |
| 2011/0060359 A1 | 3/2011 | Hannes et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0184456 A1 | 7/2011 | Grandfield et al. |
| 2011/0196414 A1* | 8/2011 | Porter .................. A61B 17/221 |
| | | 606/200 |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0276120 A1 | 11/2011 | Gilson et al. |
| 2011/0319917 A1 | 12/2011 | Ferrera et al. |
| 2012/0022572 A1* | 1/2012 | Braun .............. A61B 17/12022 |
| | | 606/194 |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0065660 A1 | 3/2012 | Ferrera et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0123466 A1 | 5/2012 | Porter et al. |
| 2012/0143237 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1* | 12/2013 | Brady ............ A61B 17/320725 |
| | | 606/200 |
| 2014/0005712 A1 | 1/2014 | Martin |
| 2014/0005713 A1 | 1/2014 | Bowman |
| 2014/0046359 A1 | 2/2014 | Bowman et al. |
| 2014/0121672 A1 | 5/2014 | Folk |
| 2014/0128905 A1 | 5/2014 | Molaei |
| 2014/0134654 A1 | 5/2014 | Rudel et al. |
| 2014/0135812 A1 | 5/2014 | Divino et al. |
| 2014/0142598 A1 | 5/2014 | Fulton, III |
| 2014/0180122 A1 | 6/2014 | Stigall et al. |
| 2014/0180377 A1 | 6/2014 | Bose et al. |
| 2014/0180397 A1 | 6/2014 | Gerberding et al. |
| 2014/0194911 A1 | 7/2014 | Johnson et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0243881 A1 | 8/2014 | Lees et al. |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1 | 10/2014 | Dacuycuy et al. |
| 2014/0330302 A1 | 11/2014 | Fekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0032144 A1* | 1/2015 | Holloway .................. A61F 2/01 |
| | | 606/200 |
| 2015/0080937 A1 | 3/2015 | Davidson |
| 2015/0112376 A1* | 4/2015 | Molaei ............. A61B 17/22031 |
| | | 606/200 |
| 2015/0133990 A1 | 5/2015 | Davidson |
| 2015/0150672 A1* | 6/2015 | Ma .................. A61B 17/12036 |
| | | 606/200 |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm |
| 2015/0352325 A1 | 12/2015 | Quick |
| 2015/0359547 A1 | 12/2015 | Vale et al. |
| 2015/0366650 A1 | 12/2015 | Zi et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0100928 A1 | 4/2016 | Lees et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |

(56) References Cited

U.S. PATENT DOCUMENTS

| | | |
|---|---|---|
| 2016/0256180 A1 | 9/2016 | Vale et al. |
| 2016/0303381 A1 | 10/2016 | Pierce et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero |
| 2017/0079680 A1 | 3/2017 | Bowman |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1* | 5/2017 | Ma .................... A61M 25/0021 |
| 2017/0143465 A1 | 5/2017 | Ulm, III |
| 2017/0147765 A1 | 5/2017 | Mehta |
| 2017/0150979 A1 | 6/2017 | John |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |
| 2018/0263650 A1 | 9/2018 | Iwanami et al. |
| 2018/0325537 A1 | 11/2018 | Shamay et al. |
| 2018/0326024 A1 | 11/2018 | Prochazka et al. |
| 2018/0344338 A1 | 12/2018 | Brady et al. |
| 2019/0000492 A1 | 1/2019 | Casey et al. |
| 2019/0015061 A1 | 1/2019 | Liebeskind et al. |
| 2019/0167284 A1 | 6/2019 | Friedman et al. |
| 2019/0239907 A1 | 8/2019 | Brady et al. |
| 2019/0292273 A1 | 9/2019 | Hanotin et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0009150 A1 | 1/2020 | Chamorro Sanchez |
| 2020/0100804 A1 | 4/2020 | Casey et al. |
| 2020/0297364 A1 | 9/2020 | Choe et al. |

FOREIGN PATENT DOCUMENTS

| | | |
|---|---|---|
| CN | 102307613 A | 1/2012 |
| CN | 102596098 A | 7/2012 |
| CN | 103764049 A | 4/2014 |
| CN | 104042304 A | 9/2014 |
| CN | 105208950 A | 12/2015 |
| CN | 105662532 A | 6/2016 |
| CN | 205359559 U | 7/2016 |
| CN | 107530090 A | 1/2018 |
| CN | 208582467 U | 3/2019 |
| DE | 202009001951 U1 | 3/2010 |
| DE | 102009056450 A1 | 6/2011 |
| DE | 102010010849 A1 | 9/2011 |
| DE | 102010014778 A1 | 10/2011 |
| DE | 102010024085 A1 | 12/2011 |
| DE | 102011014586 B3 | 9/2012 |
| EP | 2301450 A1 | 3/2011 |
| EP | 1153581 A1 | 11/2011 |
| EP | 2438891 A1 | 4/2012 |
| EP | 2628455 A1 | 8/2013 |
| EP | 3156004 A1 | 4/2017 |
| GB | 2427554 A | 1/2007 |
| GB | 2494820 A | 3/2013 |
| JP | 09-19438 A | 1/1997 |
| JP | 2014-511223 A | 5/2014 |
| JP | 2014-525796 A | 10/2014 |
| JP | 2016-513505 A | 5/2016 |
| JP | 2019-526365 A | 9/2019 |
| WO | WO 94/24926 A1 | 11/1994 |
| WO | WO 97/27808 A1 | 8/1997 |
| WO | WO 97/38631 A1 | 10/1997 |
| WO | WO 99/20335 A1 | 4/1999 |
| WO | WO 99/56801 A2 | 11/1999 |
| WO | WO 99/60933 A1 | 12/1999 |
| WO | WO 01/21077 A1 | 3/2001 |
| WO | WO 02/02162 A2 | 1/2002 |
| WO | WO 02/11627 A2 | 2/2002 |
| WO | WO 02/43616 A2 | 6/2002 |
| WO | WO 02/070061 A1 | 9/2002 |
| WO | WO 02/094111 A2 | 11/2002 |
| WO | WO 03/002006 A1 | 1/2003 |
| WO | WO 03/030751 A1 | 4/2003 |
| WO | WO 03/051448 A2 | 6/2003 |
| WO | WO 2004/028571 A2 | 4/2004 |
| WO | WO 2004/056275 A1 | 7/2004 |
| WO | WO 2005/000130 A1 | 1/2005 |
| WO | WO 2005/027779 A2 | 3/2005 |
| WO | WO 2006/021407 A2 | 3/2006 |

(56) References Cited

FOREIGN PATENT DOCUMENTS

| | | |
|---|---|---|
| WO | WO 2006/031410 A2 | 3/2006 |
| WO | WO 2006/107641 A2 | 10/2006 |
| WO | WO 2006/135823 A2 | 12/2006 |
| WO | WO 2007/054307 A2 | 5/2007 |
| WO | WO 2007/068424 A2 | 6/2007 |
| WO | WO 2008/034615 A2 | 3/2008 |
| WO | WO 2008/051431 A1 | 5/2008 |
| WO | WO 2008/131116 A1 | 10/2008 |
| WO | WO 2008/135823 A1 | 11/2008 |
| WO | WO 2009/031338 A1 | 3/2009 |
| WO | WO 2009/076482 A1 | 6/2009 |
| WO | WO 2009/086482 A1 | 7/2009 |
| WO | WO 2009/105710 A1 | 8/2009 |
| WO | WO 2010/010545 A1 | 1/2010 |
| WO | WO 2010/046897 A1 | 4/2010 |
| WO | WO 2010/075565 A2 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | WO 2011/106426 A1 | 9/2011 |
| WO | WO 2011/110316 A1 | 9/2011 |
| WO | WO 2011/135556 A1 | 11/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/110619 A1 | 8/2012 |
| WO | WO 2012/120490 A2 | 9/2012 |
| WO | WO 2012/156924 A1 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A2 | 7/2013 |
| WO | WO 2013/187927 A1 | 12/2013 |
| WO | WO 2014/047650 A1 | 3/2014 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2015/061365 A1 | 4/2015 |
| WO | WO 2015/103547 A1 | 7/2015 |
| WO | WO 2015/134625 A1 | 9/2015 |
| WO | WO 2015/179324 A2 | 11/2015 |
| WO | WO 2015/189354 A1 | 12/2015 |
| WO | WO 2016/010995 A1 | 1/2016 |
| WO | WO 2016/089451 A1 | 6/2016 |
| WO | WO 2017/089424 A1 | 6/2017 |
| WO | WO 2017/103686 A2 | 6/2017 |
| WO | WO 2017/161204 A1 | 9/2017 |
| WO | WO 2020/039082 A1 | 2/2020 |
| WO | WO 2021/113302 A1 | 6/2021 |

\* cited by examiner

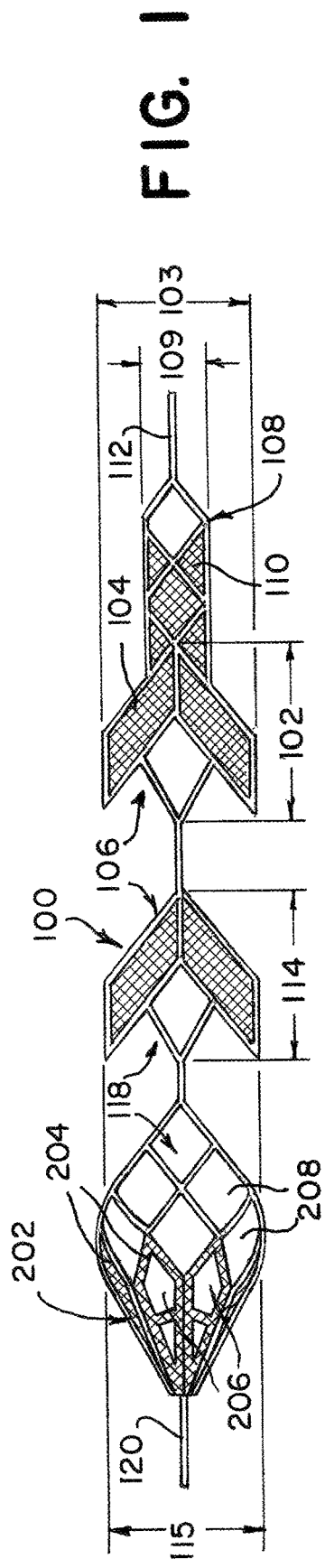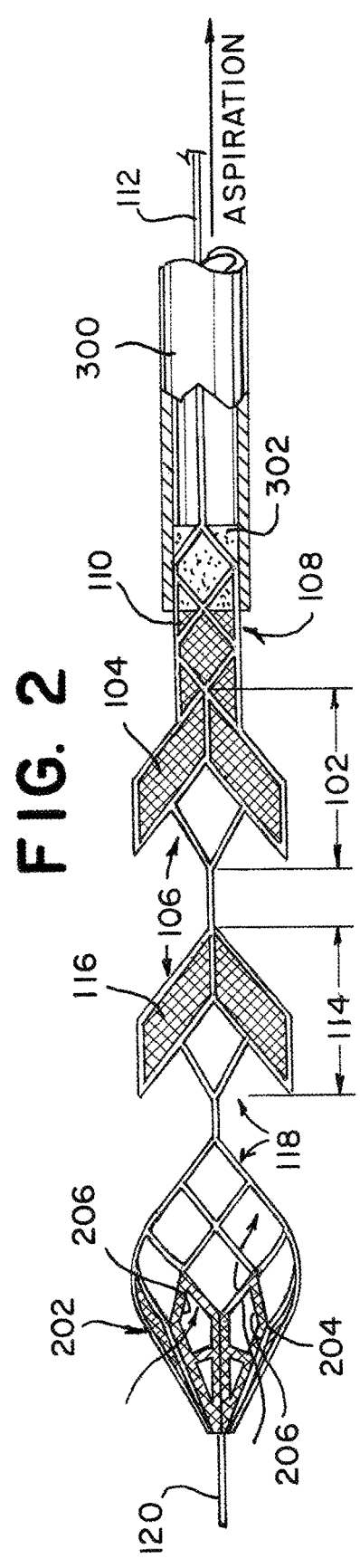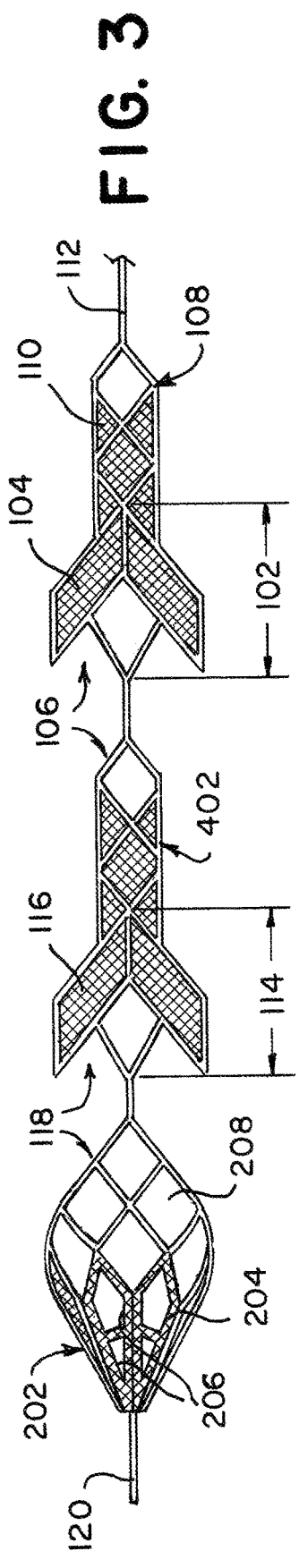

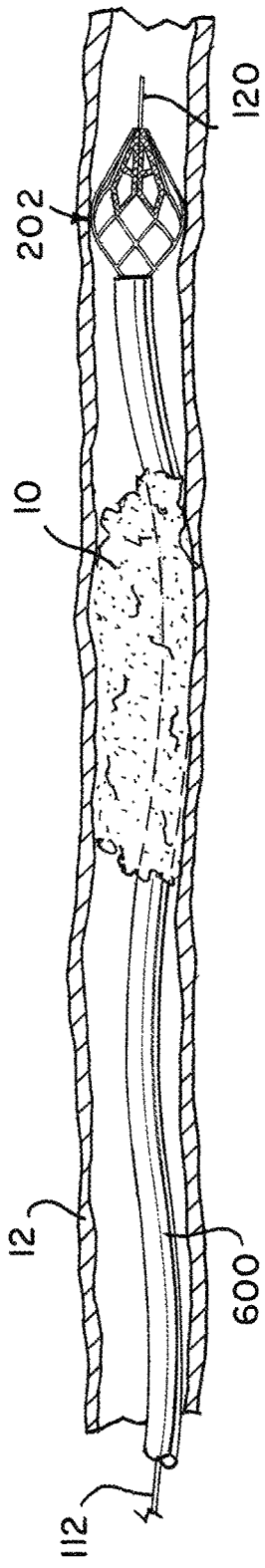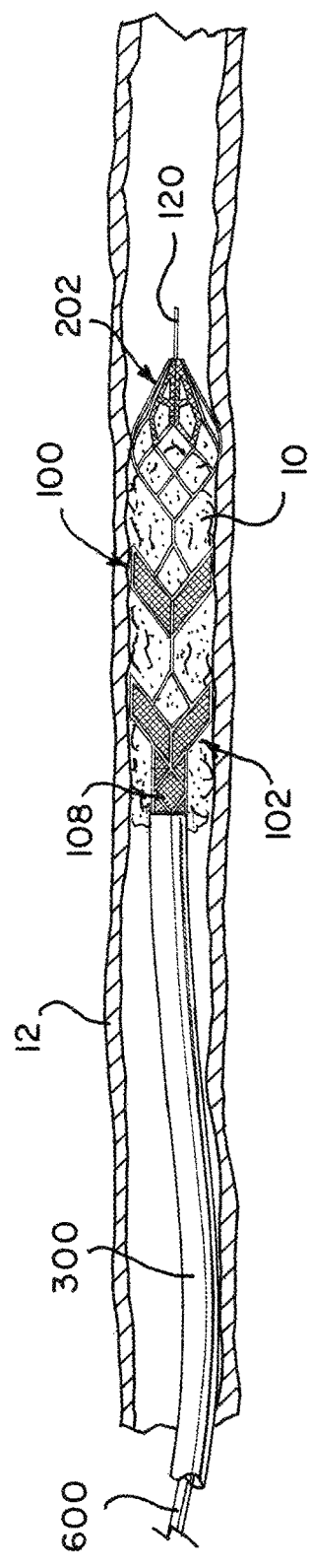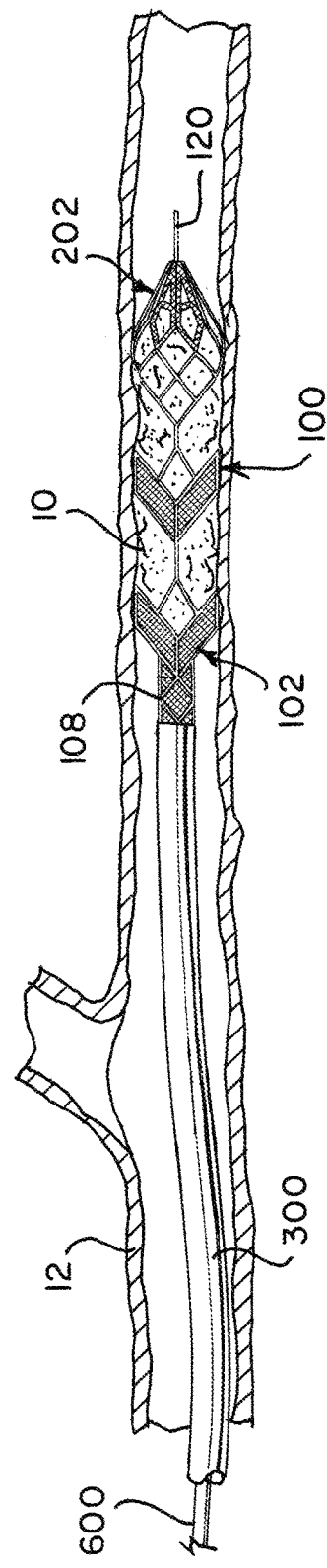

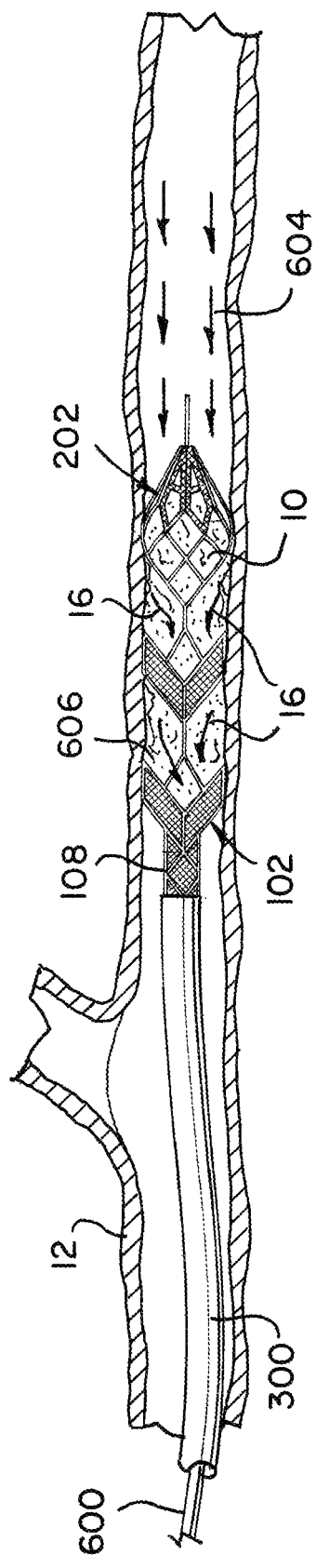
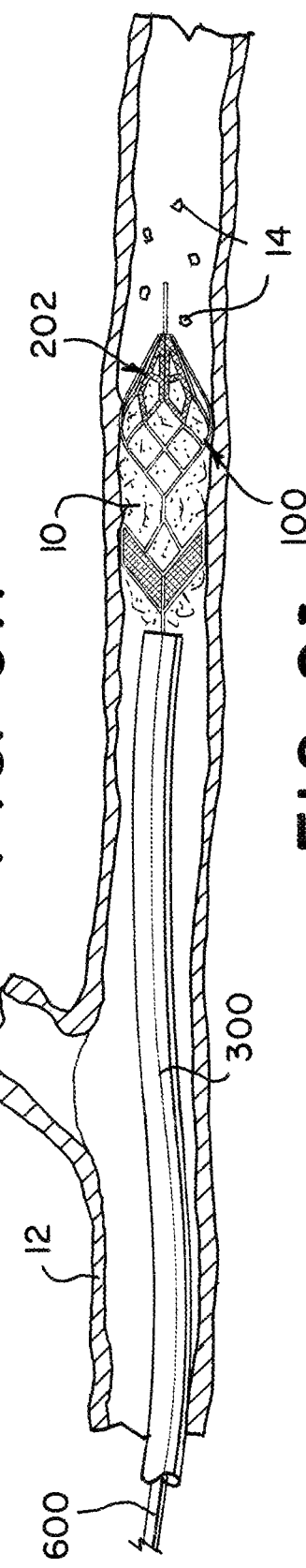
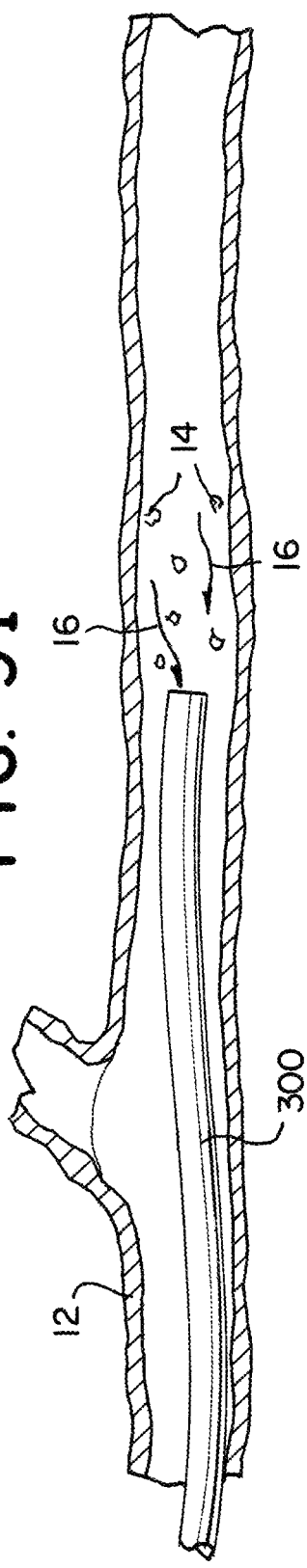

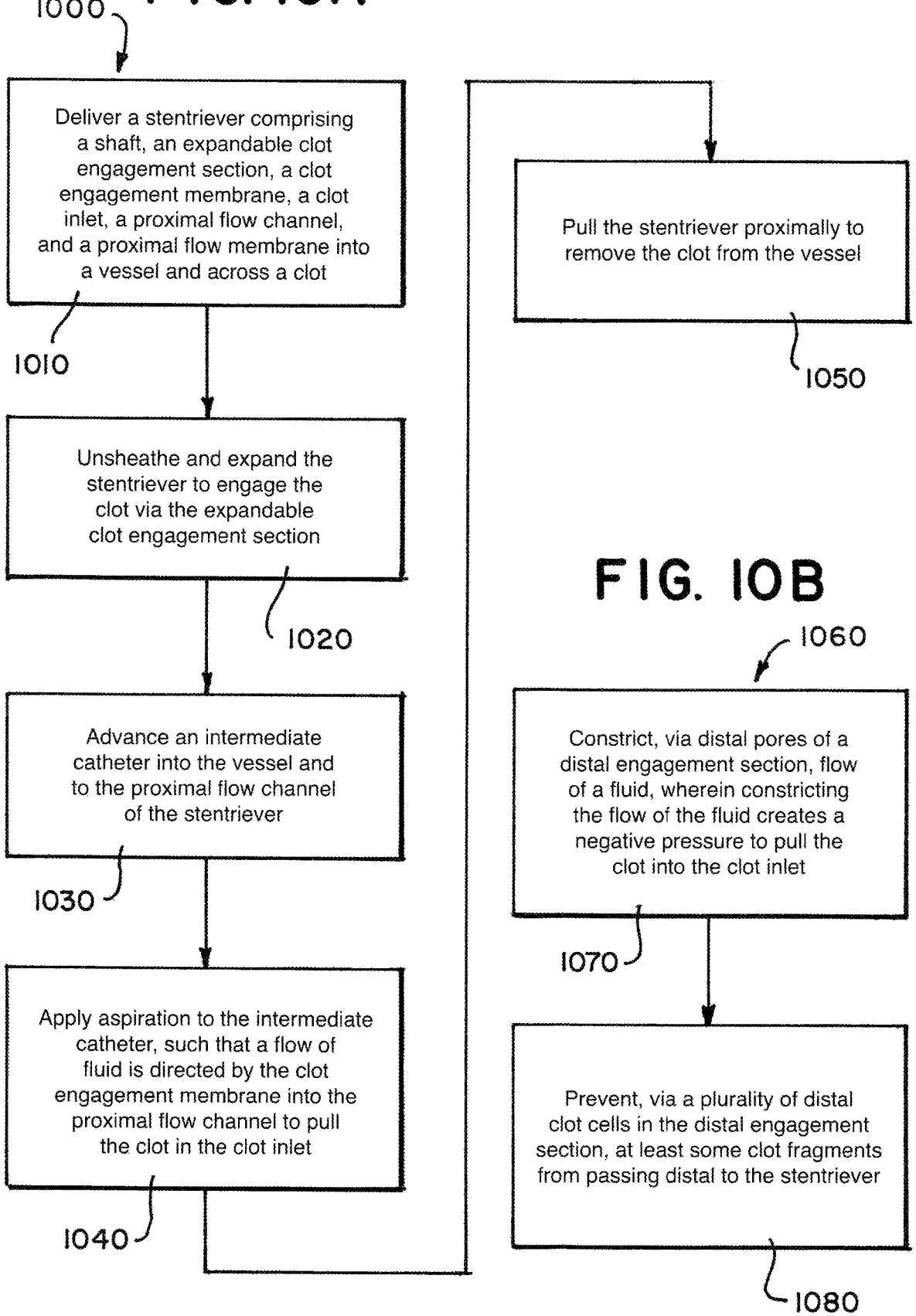

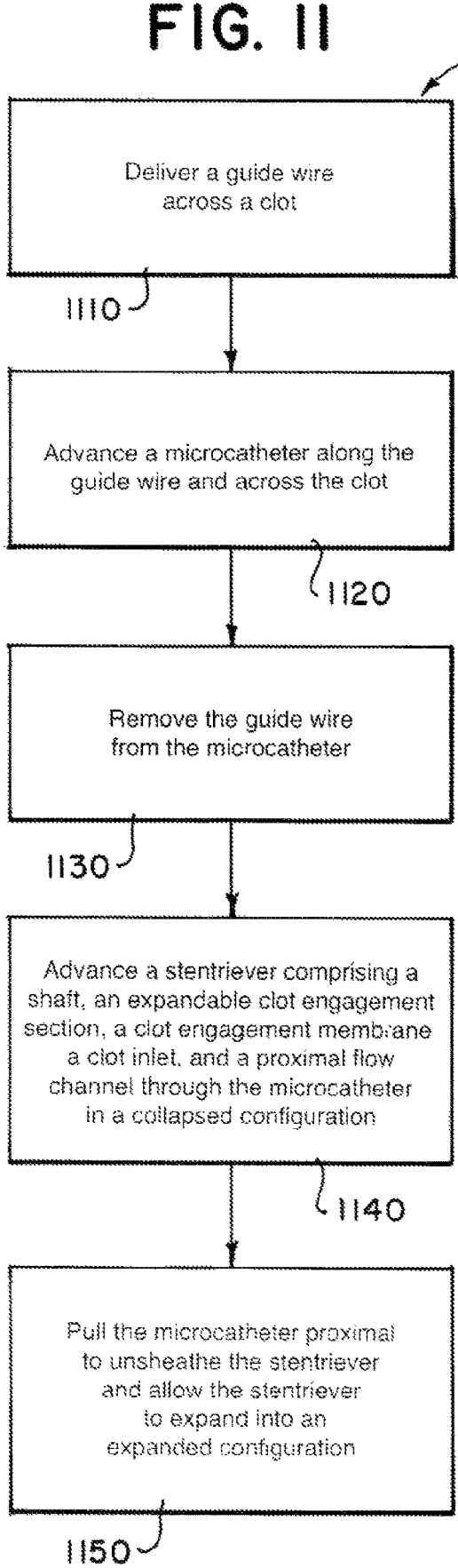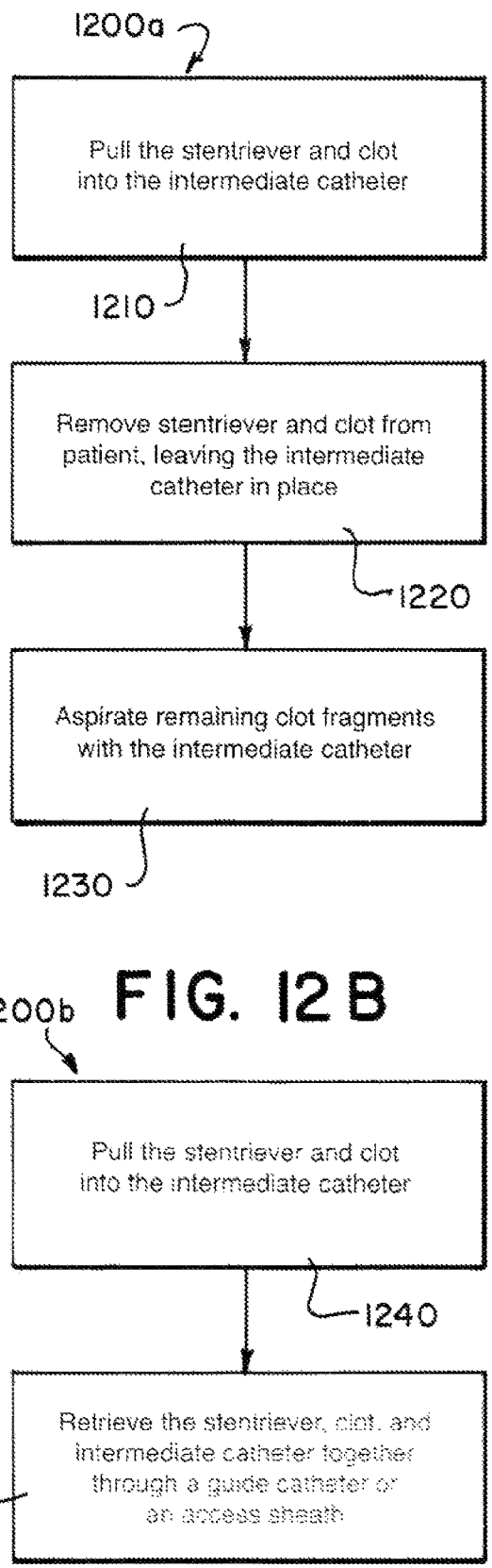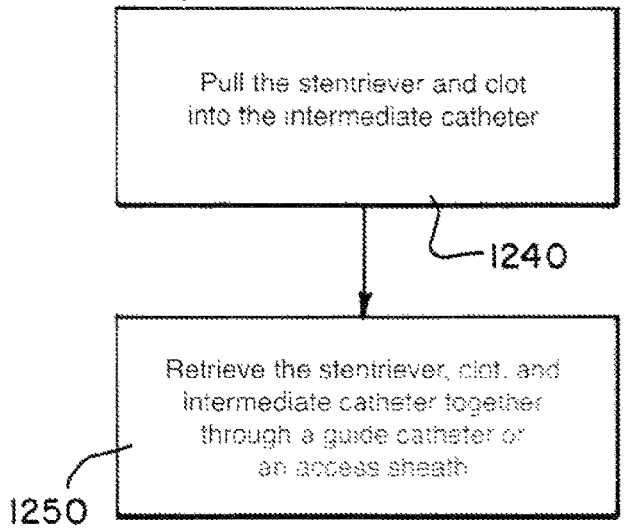

STENTRIEVER DEVICES FOR REMOVING AN OCCLUSIVE CLOT FROM A VESSEL AND METHODS THEREOF

FIELD OF INVENTION

The present disclosure generally relates to devices intended for removing acute blockages from blood vessels, and more particularly, to stentriever devices with membranes to direct fluid aspiration and enhance the stentriever's grip on an occlusive clot.

BACKGROUND

There are significant challenges associated with designing clot removal devices that can deliver high levels of performance. One challenge stems from the nature of the vasculature around an occlusive clot, which is often fragile and delicate. Neurovascular vessels, for example, are more fragile than similarly sized vessels in other parts of the body. Applying excessive tensile forces to these vessels could result in perforations and hemorrhage. Another challenge stems from the wide range of morphologies and consistencies of occlusive clots. Long strands of softer clot material may tend to lodge at bifurcations or trifurcations, resulting in multiple vessels being simultaneously occluded over significant lengths. More mature and organized clot material is likely to be less compressible than softer, fresher clot material, and under the action of blood pressure it may distend the compliant vessel in which the clot is lodged.

Stent-like clot retrievers, otherwise known as stentrievers, are being increasingly used to remove clots, as the devices show promise in dealing with some of the challenges described above. Stentrievers are self-expanding devices, similar in appearance to a stent attached to the end of a long shaft, which are advanced through a microcatheter and deployed across clot obstructions in order to trap and retrieve the clot. Many stentrievers rely on a pinning mechanisms to grab the clot by trapping the clot between the self-expanding, stent-like body and the vessel wall. Current stentrievers have a number of disadvantages that decrease the utility of the devices.

One disadvantage is that many stentrievers rely exclusively on an outward radial force (RF) to retain a grip on the clot. If the RF is too low the stentriever may lose its grip on the clot, but if the RF is too high the stentriever may damage the vessel wall and/or may require excessive force to withdraw the stentriever from the vessel. Stentrievers that apply sufficient RF to deal with all clot types may cause vessel trauma and serious patient injury, and stentrievers that apply low RF to remain atraumatic may not effectively handle all clot types.

Another disadvantage with current stentrievers is with the pinning mechanism itself. Stentrievers that rely exclusively on pinning clots against a vessel wall may not restrain the clot effectively when passing a branch vessel or when passing into a vessel that is larger than the fully expanded diameter of the stentriever. These and other disadvantages exist with previous stentriever devices. Accordingly, there is an ongoing need for an improved stentriever device that can improve grip on an occlusive clop without increasing the outward RF on the clot, thereby protecting the surrounding vasculature.

SUMMARY

Examples presented herein include stentrievers with membranes to direct fluid aspiration and enhance the stentriever's grip on an occlusive clot. The stentriever design described herein can include a membrane cover on the proximal end which can be sized to form a seal with the tip of an intermediate catheter. Clot engagement sections and/or a distal engagement section of the stentriever can also include a full or partial membrane covering to control the direction of aspiration and/or areas where the aspiration applies suction to the thrombus or clot. The membranes can be used to direct the aspiration so as to pull the clot deeper into the clot engagement sections of the stentriever, thereby improving grip on the clot. The design can also increase the effectiveness of clot fragment protection for friable clots by providing pores and/or clot cells in a distal engagement section.

An example stentriever can include a shaft extending between a proximal end and a distal end. A first expandable clot engagement section can extend from the shaft. The stentriever can include a proximal flow channel that is positioned proximal to the first expandable clot engagement section. The proximal flow channel can include a membrane covering to direct an aspiration from the first expandable clot engagement section and through the proximal flow channel. The stentriever can comprise a collapsed configuration to be inserted into a microcatheter and include an expanded configuration for exerting an outward radial force on an occlusive clot.

The first expandable clot engagement section can include a first clot inlet to capture the clot. The first clot inlet can be positioned on the stentriever distal to the first expandable clot engagement section.

The proximal flow channel can include a collapsed configuration to be inserted into a microcatheter, and the proximal flow channel can include an expanded configuration to exert an outward radial force on an intermediate catheter. In the expanded configuration, the proximal flow membrane can engage with an inner surface of the intermediate catheter at a proximal seal area do direct aspiration flow.

The first expandable clot engagement section can include a first clot engagement membrane directing the aspiration into the first expandable clot engagement section.

The stentriever can include a second expandable clot engagement section that extends from the shaft. The second expandable clot engagement section can be positioned distal to the first expandable clot engagement section.

The second expandable clot engagement section can include a second clot engagement membrane to direct the aspiration into the second expandable clot engagement section.

The second expandable clot engagement section can include a second clot inlet to capture the clot. The second clot inlet can be positioned on the stentriever distal to the second expandable clot engagement section.

The stentriever can include an intermediate flow channel positioned proximal to and adjacent the second expandable clot engagement section. The intermediate flow channel can direct the aspiration from the second expandable clot engagement section to the first expandable clot engagement section.

The stentriever can include a distal engagement section positioned distal to the first expandable clot engagement section. The distal engagement section can extend from the shaft. The distal engagement section can include a plurality of distal clot cells to capture clot fragments, such that the clot fragments do not pass distal to the stentriever.

The distal engagement section can include a distal membrane. The distal membrane can include distal pores that can constrict the flow of aspiration into the distal engagement section. The constriction of aspirate flow through the distal engagement section can create a negative pressure around the first and/or second expandable clot engagement sections to further pull the clot into the engagement sections.

The first expandable clot engagement section can further include a first clot inlet capturing the clot. A distal membrane can constrict flow from the distal engagement section to the proximal flow channel to create a negative pressure at the first expandable clot engagement section, thereby pulling the clot into the first clot inlet.

An example system for removing a clot from a vessel can include a stentriever. The stentriever can include a shaft extending between a proximal end and a distal end. The stentriever can include a first expandable clot engagement section extending from the shaft. The stentriever can include a proximal flow channel positioned proximal to and adjacent the first expandable clot engagement section. The proximal flow channel can include a proximal flow membrane. The system can further include an intermediate catheter. The stentriever can have a collapsed configuration to be inserted into a microcatheter, and the stentriever can have an expanded configuration to expand in a vessel. In the expanded configuration, the proximal flow cannel can exert a radial force on the intermediate catheter, and the proximal flow membrane can seal against the inner surface of the intermediate catheter. The aspiration can be directed from the first expandable clot engagement section, through the proximal flow channel, and into the intermediate catheter.

The first expandable clot engagement section can include a first clot inlet to capture a clot within the vessel.

The first expandable clot engagement section can include a first clot engagement membrane. The first clot engagement membrane can direct an aspiration into the first expandable clot engagement section.

The stentriever can further include a second expandable clot engagement section extending from the shaft. The second expandable clot engagement section can be positioned distal to the first expandable clot engagement section. The second expandable clot engagement section can further include a second clot inlet for capturing the clot.

The stentriever can further include an intermediate flow channel positioned proximal to and adjacent the second expandable clot engagement section. The intermediate flow channel can direct the aspiration from the second expandable clot engagement section to the first expandable clot engagement section.

The second expandable clot engagement section can include a second clot engagement membrane directing the aspiration into the second expandable clot engagement section.

The stentriever can include a distal engagement section positioned distal to the first expandable clot engagement section and extending from the shaft.

The distal engagement section can include a plurality of distal clot cells for capturing clot fragments.

The distal engagement section can include a distal membrane. The distal membrane can include distal pores that constrict flow of the aspiration into the distal engagement section. The constriction of aspirate flow through the distal engagement section can create a negative pressure around the first and/or section expandable clot engagement sections to further pull the clot into the engagement sections.

The distal membrane can include distal flow aperture directing the aspiration into the distal engagement section. The distal flow aperture can be a partial opening in the distal engagement section that constricts a flow of the aspirate into the distal engagement section. The constriction of aspirate flow through the distal engagement section can create a negative pressure around the first and/or section expandable clot engagement sections to further pull the clot into the engagement sections.

An example method for removing a clot from a vessel can include delivering a stentriever into the vessel and across the clot. The stentriever can include a shaft extending between a proximal end and a distal end. The stentriever can include an expandable clot engagement section extending from the shaft. The expandable clot engagement section can include a clot engagement membrane for directing a fluid into the expandable clot engagement section and a clot inlet. The stentriever can include a proximal flow channel positioned proximal to and adjacent the expandable clot engagement section. The proximal flow channel can include a proximal flow membrane. The proximal flow membrane can direct the fluid from the expandable clot engagement section and to the proximal flow channel. The method can include expanding the stentriever so that the expandable clot engagement section expands and exerts a radial force on the clot to engage the clot. The method can include advancing an intermediate catheter into the vessel and to the proximal flow channel. The proximal flow membrane can seal to an inner surface of the intermediate catheter. The method can include applying aspiration to the intermediate catheter such that a flow of the fluid is directed by the clot engagement membrane and into the proximal flow channel to capture the clot in the clot inlet. The method can include pulling the stentriever proximally to remove the clot from the vessel.

The stentriever can include a distal engagement section positioned distal to the expandable clot engagement section and extending from the shaft. The distal engagement section can include a distal membrane with a plurality of distal pores. The method can further include constricting, via the distal membrane, the flow of the fluid through the plurality of distal pores and into the distal engagement section. The constriction of the fluid flow can create a negative pressure to pull the clot into the clot inlet.

The distal engagement section can include a plurality of distal clot cells. The method can include preventing, via the plurality of distal clot cells, at least some clot fragments from passing distal to the stentriever.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1 is a side-view illustration of an exemplary stentriever, according to aspects of the present invention;

FIG. 2 is a side-view illustration of an exemplary stentriever interacting with an intermediate catheter, according to aspects of the present invention;

FIG. 3 is a side-view illustration of an exemplary stentriever having an intermediate flow channel, according to aspects of the present invention;

FIGS. 9A-9I depict an exemplary method of deploying a stentriever and removing an occlusive clot from a vessel, according to aspects of the present invention; FIG. 9A depicts a clot occluding a vessel; FIG. 9B a depicts a guide wire fed through the vessel and across the clot 10; FIG. 9C depicts a stentriever advanced through the microcatheter distal to the clot;

FIG. 9D depicts the microcatheter retracted proximally while the position of the stentriever is maintained; FIG. 9E depicts an intermediate catheter advanced to a proximal flow channel of the stentriever; FIG. 9F depicts aspiration being applied to the proximal flow channel via the intermediate catheter; FIG. 9G depicts a flow of the aspirate into the stentriever; FIG. 9H depicts the stentriever partially retracted into the intermediate catheter; and FIG. 9I depicts the stentriever retracted into the intermediate;

FIG. 10A is a flowchart depicting a method of removing a clot from a vessel, according to aspects of the present invention;

FIG. 10B is a flowchart depicting a method of using a distal engagement section to constrict flow and prevent clot fragments from passing distal to the stentriever, according to aspects of the present invention;

FIG. 11 is a flowchart depicting a method of deploying a stentriever, according to aspects of the present invention;

FIG. 12A is a flowchart depicting a method of removing a clot from a patient, according to aspects of the present invention; and FIG. 12B is a flowchart depicting a method of removing a clot from a patient, according to aspects of the present invention.

DETAILED DESCRIPTION

Figure 4:
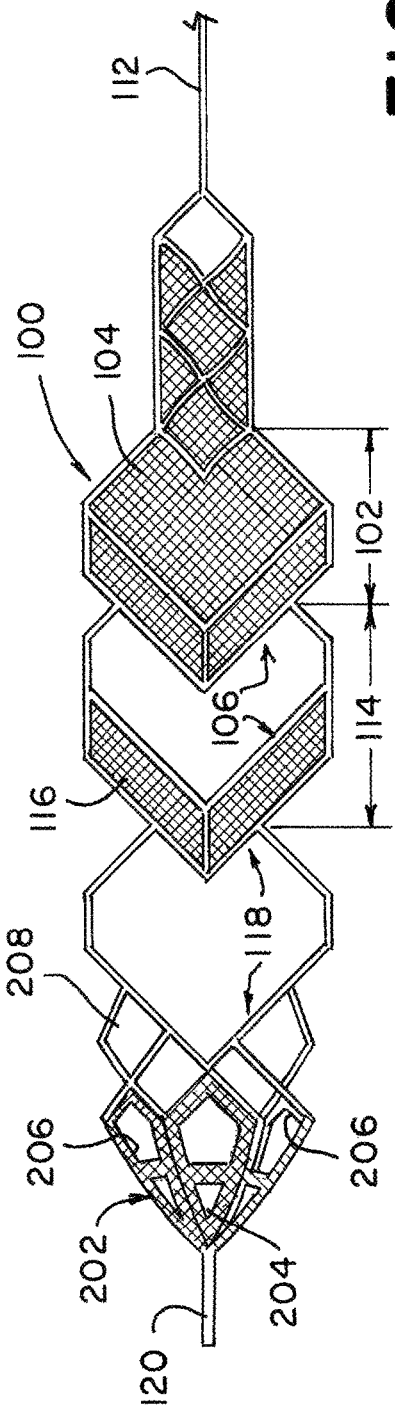
FIG. 4 is a top-view illustration of an exemplary stentriever, according to aspects of the present invention.

Aspects of the present invention relate to a stentriever that includes a full or partial membrane cover on the proximal end of the device that is sized so that the proximal section can form a seal with the tip of an intermediate catheter. The stentriever device can include one or more expandable clot engagement sections and/or a distal engagement section. The expandable clot engagement sections and the distal engagement section can also include a membrane covering to control the direction of aspirate, and thus the direction of suction upon a thrombus or clot. The direction of aspirate can act to pull a clot deeper into inlet windows (i.e., clot inlets) of the expandable clot engagement sections. The direction of aspirate and suction can improve clot grip, decrease dislodgement of a clot within the stentriever, and increase retention of the clot when the clot is pulled into the intermediate catheter, access or guide catheter, or access sheath. In some examples, the design can also increase the effectiveness of clot-fragment protection for friable clots by providing antegrade flow through the distal engagement section.

Turning to the figures, FIG. 1 is a side-view illustration of an exemplary stentriever 100, according to aspects of the present invention. In some examples, this expanded configuration is exemplary of a stentriever 100 that is deployed into vessel. In some examples, a stentriever 100 can include a first expandable clot engagement section 102. The first expandable clot engagement section 102 can be an expandable feature that has a collapsed configuration and an expanded configuration, the expanded configuration being shown in FIG. 1. In a collapsed configuration, the first expandable clot engagement section 102 can be inserted into a microcatheter for deployment into a vessel and across a clot. It is contemplated that a diameter 103 of a first expandable clot engagement section 102 can be less than approximately 1.75 mm when the first expandable clot engagement section 102 is in a collapsed configuration. For example, ordinary microcatheters can have inner diameters of from 0.015 inches to 0.065 inches (approximately 0.38 mm to approximately 1.65 mm), and it is contemplated that a diameter 103 of a first expandable clot engagement section 102 can fall within these typical ranges. In the expanded configuration, the first expandable clot engagement section 102 can open to engage a clot within vessel by exerting a radial force upon the clot. A first expandable clot engagement section 102 can be manufactured according to the size of the vasculature in which the stentriever 100 is being deployed. It is contemplated that the diameter 103 of the expanded first expandable clot engagement section 102 can range from approximately 1.5 mm to approximately 7.0 mm, for example, and not limitation, approximately 4.00 mm. As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

The first expandable clot engagement section 102 can be made from a material capable of recovering its shape automatically once unsheathed into its expanded configuration. The material could be in many forms such as wire, strip, sheet, or tube. In some examples, the first expandable clot engagement section 102 can include, but is not limited to, Nitinol, stainless steel, MP35N, tungsten, and/or the like or any combination or alloy thereof. In some examples, the material can be made from a memory shape material, such as Nitinol, and the expanded configuration for a first expandable clot engagement section 102 can be made by heat setting the material to the expanded configuration.

In some examples, a stentriever 100 can include a first clot engagement membrane 104 attached to the first expandable clot engagement section 102. The first clot engagement membrane 104 can be a full or partial covering of the first expandable clot engagement section 102 to direct a suction and/or aspirate into the first expandable clot engagement section 102. The material for the first clot engagement membrane 104 can include silicon, polyurethane, polypropylene, polyethersulfone, and/or the like. In some examples, the material for the first clot engagement membrane 104 can be pliable such that the material can be opened as the first expandable clot engagement section 102 opens from a collapsed configuration to an expanded configuration.

A first expandable clot engagement section 102 can include a first clot inlet 106. A first clot inlet 106 can be an opening distal to the first expandable clot engagement section 102 that is not covered by a first clot engagement membrane 104 and provides an area for an occlusive clot to be pulled into the first expandable clot engagement section 102. As will be appreciated, the examples described herein provide a way to capture a clot without relying exclusively on the radial force applied by the expandable sections of the stentriever 100. As suction is applied to the stentriever 100, the clot can be directed along with the flow of aspirate into the first clot inlet 106 via the first clot engagement membrane 104, and continued suction can provide improved grip on the clot.

A stentriever 100 can include a proximal flow channel 108. The proximal flow channel 108 can be positioned proximal to the first expandable clot engagement section 102. The proximal flow channel 108 can have a collapsed configuration and an expanded configuration, similar to the first expandable clot engagement section 102 described above. It is contemplated that the diameter 109 of a proximal flow channel 108 in a collapsed configuration can, similar to the first expandable clot engagement section 102, be less than approximately 1.75 mm so as to fit within a microcatheter for delivery into the vessel.

The proximal flow channel 108 can be a braided tube, laser cut metallic tube, laser cut polymeric tube and/or the like. In some examples, the proximal flow channel 108 can include, but is not limited to, materials such as Nitinol, stainless steel, MP35N, tungsten, and/or the like or any combination or alloy thereof. In some examples, the material can be made from a memory shape material, such as Nitinol, and the expanded configuration for a proximal flow channel 108 can be made by heat setting the material to the expanded configuration.

The proximal flow channel 108 can include a proximal flow membrane 110. The proximal flow membrane 110 can cover an outer surface of the proximal flow channel 108 at a position proximal to the first expandable clot engagement section 102. The proximal flow membrane 110 can direct the flow of aspirate from the first expandable clot engagement section 102 and through the proximal flow channel 108. The flow of the aspirate through the proximal flow channel 108 can increase the suction around the first expandable clot engagement section 102 so as to pull a clot deeper into first clot inlet 106. The material for the proximal flow membrane 110 can be silicon, polyurethane, polypropylene, polyethersulfone, and/or the like. In some examples, the material for the proximal flow membrane 110 can be pliable such that the material can be opened as the proximal flow channel 108 opens from a collapsed configuration to an expanded configuration.

In some examples, the proximal flow channel 108 can be opened into its expanded configuration while deployed into the vessel. Once expanded, the proximal flow channel 108 can have a diameter 109 of approximately equal to the inner diameter of an intermediate or access catheter. For example, once deployed, an intermediate catheter can be advanced into position after the stentriever 100 is deployed within a clot. The intermediate catheter can be directed to the proximal flow channel 108. In some examples, the proximal flow membrane 110 can form a seal with the inner surface of the intermediate catheter. The seal can allow aspiration to be drawn from the first expandable clot engagement section 102, through the membrane-covered proximal flow channel 108, and into the intermediate catheter to further pull the clot into the first clot inlet 106. Intermediate catheters can have an inner diameter of approximately 0.040 inches to approximately 0.120 inches (approximately 1.0 mm to approximately 3.0 mm). Accordingly, it is contemplated that the diameter 109 of a proximal flow channel 108 in an expanded configuration can fall within those ranges.

The proximal flow channel 108 can have a length suitable for engaging with an intermediate catheter which has been forwarded to the vicinity of the clot. In another embodiment, the proximal flow channel can have sufficient length to engage with an intermediate or access catheter which has been parked in the Internal Carotid Artery. It is contemplated that the length of the proximal channel can have a range of approximately 2.0 mm to 100 mm.

A stentriever 100 can include a flexible shaft 112. The shaft 112 can act as a both a delivery mechanism to feed the stentriever 100 into the vessel and as a scaffold or frame for the additional features of the stentriever 100. The expandable clot engagement sections (e.g., first expandable clot engagement section 102) for example, can be connected to and extend from the shaft 112. The shaft can be made from a flexible material, including but not limited to metals and polymers, such that the stentriever 100 can bend as the device is deployed into a vessel.

A stentriever 100 can include a second expandable clot engagement section 114. The second expandable clot engagement section 114 can extend from the shaft 112, similar to the first expandable clot engagement section 102, and be positioned distal to the first expandable clot engagement section 102 on the shaft 112. The second expandable clot engagement section 114 can be similar in all aspects to the first expandable clot engagement section 102. Though the first expandable clot engagement section 102 and second expandable clot engagement section 114 can comprise identical materials and have identical dimension, nothing requires the two sections to be identical. The second expandable clot engagement section 114 can act as a second capturing device, wherein in an expanded configuration, the second expandable clot engagement section 114 can engage the clot within vessel by exerting a radial force upon the clot. Although FIG. 1 depicts a stentriever 100 having two clot engagement section (i.e., first expandable clot engagement section 102 and second expandable clot engagement section 114), a stentriever 100 described herein is not limited to two clot engagement sections, as more than two could be provided.

In some examples, a stentriever 100 can include a second clot engagement membrane 116 attached to the second expandable clot engagement section 114. The second clot engagement membrane 116 can be a full or partial covering of the second expandable clot engagement section 114 to direct a suction and/or aspirate into the second expandable clot engagement section 114. The material for the second clot engagement membrane 116 can be similar to the materials described above for the first clot engagement membrane 104.

A second expandable clot engagement section 114 can include a second clot inlet 118. A second clot inlet 118 can be an opening distal to the second expandable clot engagement section 114 that is not covered by a second clot engagement membrane 116 and provides an area for an occlusive clot to be pulled into the second expandable clot engagement section 114. By providing a first clot inlet 106 and a second clot inlet 118, the clot can be pulled, by providing aspiration to the proximal flow channel 108, into both clot inlets 106,118 for improved grip on the clot.

A shaft 112 of a stentriever 100 can include a distal tip 120. The distal tip 120 can include a rounded and/or smooth end so as to not perforate a wall of a vessel as the stentriever 100 is being deployed within the vessel. In some examples, the distal tip 120 can include radiopaque coil or marker disposed on or in the distal tip 120 for visibility under fluoroscopy. Additional radiopaque coils or markers can be added near the expandable clot engagement sections such that a physician can view the position of the device in relation to the occlusive clot under fluoroscopy.

A stentriever 100 can include a distal engagement section 202 positioned distal to the first expandable clot engagement section 102; when a stentriever 100 includes a second expandable clot engagement section 114, the distal engagement section 202 is distal to the second section. When a physician inserts the stentriever 100 into a vessel, the stentriever 100 can be passed beyond the clot such that the distal engagement section 202 is within the vessel distal to the clot. The distal engagement section 202 can have a collapsed configuration and an expanded configuration, and the dimensions of the distal engagement section 202 in the collapsed configuration and the expanded configuration can be similar to the dimensions described above for the first expandable clot engagement section 102. As will be described below, once expanded, the distal engagement section 202 can expand to fill the cross-sectional area of the vessel and constrict fluid flow through the distal engagement section 202. The materials that can be used for a distal engagement section 202 can include, but are not limited to, Nitinol, stainless steel, MP35N, tungsten, and/or the like or any combination or alloy thereof. In some examples, the material can be made from a memory shape material, such as Nitinol, and the expanded configuration for a distal engagement section 202 can be made by heat setting the material to the expanded configuration.

A distal engagement section 202 can include a distal membrane 204. The distal membrane 204 can be a partial membrane covering of the distal end of the distal engagement section 202. The material for the distal membrane 204 can be silicon, polyurethane, polypropylene, polyethersulfone, and/or the like.

The distal membrane 204 can include one or more distal pores 206. Distal pores 206 can be holes created in the distal membrane 204 to allow flow, albeit limited flow, through the distal membrane 204. The distal pores 206 can be laser cut, stamped, or perforated holes within the material of the distal membrane 204. At least a portion of the distal pores 206 can have a length of less than 500 micrometers from one side of the distal pore 206 to the other. In the case that the distal pores 206 are circular, the circular distal pores 206 can have a diameter of less than 500 micrometers. The length and/or diameter of the distal pores 206 can be altered so as to increase or decrease the amount of flow permitted through the distal pores 206. For example, distal pores 206 can constrict (i.e., partially limit but not necessarily completely restrict) flow of aspirate through the distal engagement section 202. When suction is applied to the proximal flow channel 108 via an intermediate catheter, the constricted flow through the distal pores 206 can create an area of negative pressure between the distal engagement section 202 and the first expandable clot engagement section 102. This negative pressure can increase the suction of the clot into the first clot inlet 106, thereby improving grip on the clot. When a stentriever 100 includes a second expandable clot engagement section 114, the negative pressure provided by the constricted flow can also further pull the clot into a second clot inlet 118.

In some examples, the distal pores 206 can also serve to prevent friable-clot fragments from passing distal to the stentriever 100. As described above, clots are oftentimes fragile and delicate. When a clot is being removed from a vessel, fragments of the clot can dislodge from the body of the occlusion. The distal pores 206 provide a mechanism for preventing the loose fragments from passing distal to the stentriever 100 as the clot and device are removed from the vessel.

A distal engagement section 202 can include a plurality of distal clot cells 208 positioned proximal to the distal membrane 204. The distal clot cells 208 can be part of the frame of the distal engagement section 202. For example, the distal engagement section 202 can be a braided mesh of the materials described above, and the distal clot cells 208 can be the areas between the scaffold of the braided mesh. When the stentriever 100 is removed from the vessel, the distal clot cells 208 can help to grip the clot and prevent the clot from moving distal to the stentriever. The distal clot cells 208 can also provide a mechanism for preventing loose fragments of the clot from passing distal to the stentriever 100 as the clot and device are removed from the vessel.

FIG. 2 is a side-view illustration of an exemplary stentriever 100 interacting with an intermediate catheter 300, according to aspects of the present invention. FIG. 2 depicts an exemplary intermediate catheter 300 being positioned at a proximal flow channel 108, as described above. The intermediate catheter 300 can form a seal with the proximal flow membrane 110 at a proximal seal area 302, thereby allowing suction to be directed from the first expandable clot engagement section 102, into the proximal flow channel 108, and through the intermediate catheter 300. The intermediate catheter 300 can be advanced over the shaft 112, and the proximal end of the shaft 112 can reside within the intermediate catheter 300 when the catheter is proximate the proximal flow channel 108.

FIG. 3 is a side-view illustration of an exemplary stentriever 100 having an intermediate flow channel 402, according to aspects of the present invention. A stentriever 100 can include an intermediate flow channel 402 positioned proximal to and adjacent the second expandable clot engagement section 114. The intermediate flow channel 402 can have a collapsed configuration and an expanded configuration, similar to the configurations described above for the proximal flow channel 108. The dimensions of an intermediate flow channel 402 can also be similar to the dimensions of a proximal flow channel 108. The intermediate flow channel can be a braided tube, laser cut metallic tube, laser cut polymeric tube and/or the like. In some examples, the intermediate flow channel 402 can include, but is not limited to, materials such as Nitinol, stainless steel, MP35N, tungsten, and/or the like or any combination or alloy thereof. In some examples, the material can be made from a memory shape material, such as Nitinol, and the expanded configuration for an intermediate flow channel 402 can be made by heat setting the material to the expanded configuration.

An intermediate flow channel 402 can include a membrane, similar to the proximal flow membrane 110 described above for the proximal flow channel 108. The intermediate flow channel 402 can direct a flow of aspirate from the second expandable clot engagement section 114 to a position proximal to the second expandable clot engagement section 114. The flow of the aspirate through the intermediate flow channel 402 can be used to localize the suction upon the clot. For example, an intermediate flow channel 402 can allow the aspirate suction to be directed to the second clot inlet 118, further improving the grip on the clot. In some examples, a certain amount of open space can be disposed between the proximal end of the intermediate flow channel 402 and the first clot inlet 106 (as shown in the figure) such that the first clot inlet 106 has room to capture at least a portion of the clot.

FIG. 4 is a top-view illustration of an exemplary stentriever 100, according to aspects of the present invention. This view of a stentriever 100 provides an alternative view of the stentriever 100 shown in FIG. 1. As can be seen, the first clot inlet 106 (and the second clot inlet 118, when provided) can remain open and without a membrane covering. This allows the clot to enter the uncovered area and be captured within the inlets.

Figure 5A:
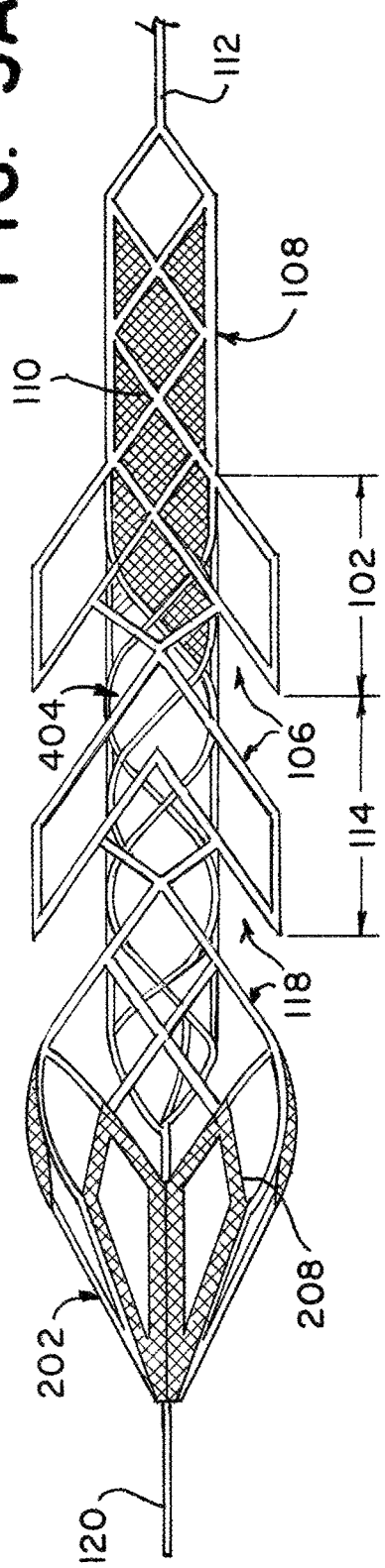
FIG. 5A is a side-view illustration of an exemplary stentriever having an inner channel, according to aspects of the present invention.

FIG. 5A is a side-view illustration of an exemplary stentriever 100 having an inner channel 404, according to aspects of the present invention. In some examples, a stentriever 100 can include an inner channel 404 that extends from the proximal end of the device to the distal engagement section 202. FIG. 5A depicts an exemplary stentriever 100 without membranes on the first expandable clot engagement section 102, the second expandable clot engagement section 114, or the distal engagement section 202. The absence of the membranes in the view provides an unobstructed view of an exemplary inner channel 404. An inner channel 404 can have a collapsed configuration and an expanded configuration, similar to the configurations described above for the proximal flow channel 108. An inner channel 404 can, in some examples, be an extension of the proximal flow channel 108. In these examples, the proximal flow channel 108—inner channel 404 combination can extend from the area proximal to the first expandable clot engagement section 102 to the distal engagement section 202. The proximal flow channel 108 can include a membrane (e.g., proximal flow membrane 110) extending to the first clot inlet 106 to help direct the aspirate and/or suction, as described herein.

Figure 5B:
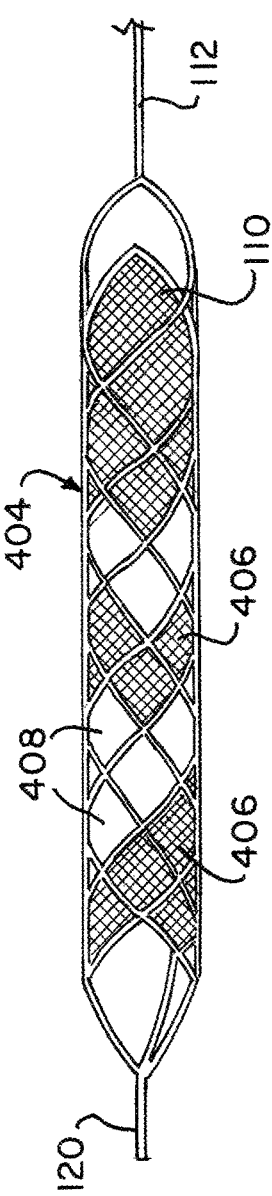
FIG. 5B is a side-view illustration of an exemplary inner channel, according to aspects of the present invention.

FIG. 5B is a side-view illustration of an exemplary inner channel 404, according to aspects of the present invention. This view shows an exemplary inner channel 404 without the expandable sections for contacting a clot, and thus provides a detailed view of the inner channel 404. An inner channel 404 can be a braided tube, laser cut metallic tube, laser cut polymeric tube and/or the like. In some examples, the inner channel 404 can include, but is not limited to, materials such as Nitinol, stainless steel, MP35N, tungsten, and/or the like or any combination or alloy thereof. In some examples, the material can be made from a memory shape material, such as Nitinol, and the expanded configuration for an inner channel 404 can be made by heat setting the material to the expanded configuration.

The inner channel 404 can include inner channel membranes 406 at positions along the length of the inner channel 404. The inner channel membranes 406 can be made similar materials as those described for the proximal flow membrane 110 above. The inner channel membranes 406 can be positioned at locations on the length of the inner channel 404 to correspond with the one or more clot engagement sections described above. For example, an inner channel membrane 406 can be positioned proximate a second expandable clot engagement section 114 (not shown in the figure) such that aspirate can be directed from the second expandable clot engagement section 114, into the inner channel membrane 406, and proximal in the device. In some examples, an inner channel membrane 406 can be provided proximate the distal engagement section 202 (not shown in the figure) to direct flow from the distal engagement section 202.

In some examples, the inner channel 404 can include a plurality of inner channel pores 408 within the surface of the inner channel 404. The inner channel pores 408 can be openings that allow fluid to flow from an area outside of the inner channel 404 to an area inside the inner channel 404. The inner channel pores 408 can extend from the proximal flow membrane 110 to the end of the inner channel 404; in examples with one or more inner channel membranes 406, the inner channel pores 408 can reside in areas not covered with membrane material. In some examples, the inner channel pores 408 can be cut, etched, drilled, or the like into the surface of the inner channel 404. In other examples, the inner channel pores 408 can be inherent features of the inner channel 404 material. For example, if an inner channel 404 is a braided tube or the like, the inner channel pores 408 can be the area between the braids of the material. The inner channel pores 408 can serve to prevent large clot fragments from entering the inner channel 404, thereby preventing the stentriever 100 from clogging. Clogging of the proximal end of the stentriever 100 could degrade the suction described herein that improves the grip on the clot. It is contemplated that the inner channel pores 408 can have a length and/or diameter (depending on the shape of the particular inner channel pore 408) that is from approximately 200 micrometers to approximately 1.50 mm (e.g., from approximately 200 micrometers to approximately 500 micrometers; from approximately 500 micrometers to approximately 800 micrometers; from approximately 800 micrometers to approximately 1.20 mm; or from approximately 1.20 mm to approximately 1.50 mm). These dimensions can prevent large clot fragments from entering the inner channel 404 and clogging the suction but can also allow small fragments to be aspirated and removed from the area (e.g., through the proximal flow channel 108 and intermediate catheter 300).

Figure 6:
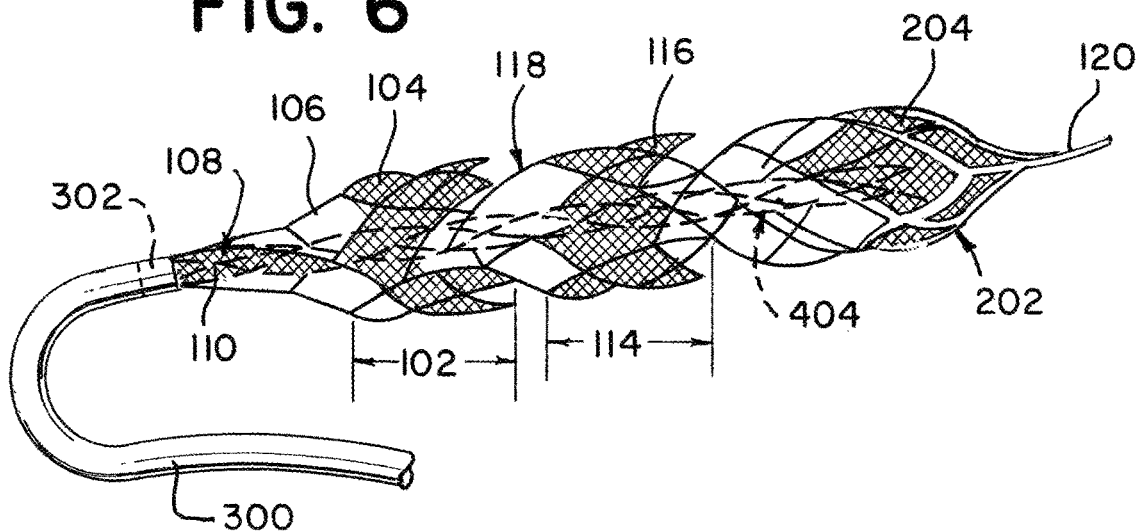
FIG. 6 is a perspective-view illustration of an exemplary stentriever with a full-length inner channel, according to aspects of the present invention.

FIG. 6 is a perspective-view illustration of an exemplary stentriever 100 with a full-length inner channel 404, according to aspects of the present invention. The exemplary stentriever 100 in FIG. 6 shows that the examples shown in FIGS. 1-5A are merely exemplary and are not inclusive of all designs contemplated herein. In some examples, a stentriever 100 can include an inner channel 404 that extends from the proximal flow channel 108 to the distal engagement section 202. It is also contemplated that an inner channel 404 can extend only partially across the length of the device, for example only to a second expandable clot engagement section 114 (or a third section, etc.). FIG. 6 also shows an example stentriever 100 wherein only the proximal flow channel 108 includes a membrane (i.e., proximal flow membrane 110), while the remainder of the length of the inner channel 404 does not include a membrane, which is in accordance with some examples.

Figure 7A:
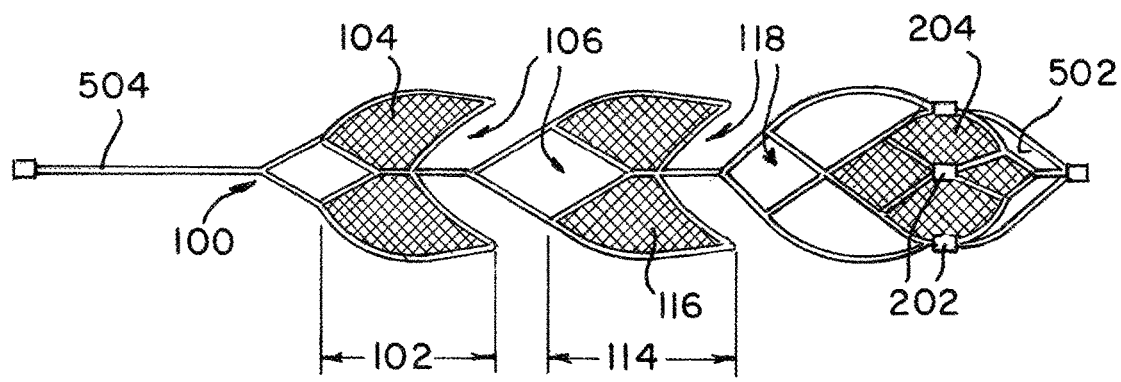
FIG. 7A is a side-view illustration of an exemplary frame for a stentriever, according to aspects of the present invention.
Figure 7B:
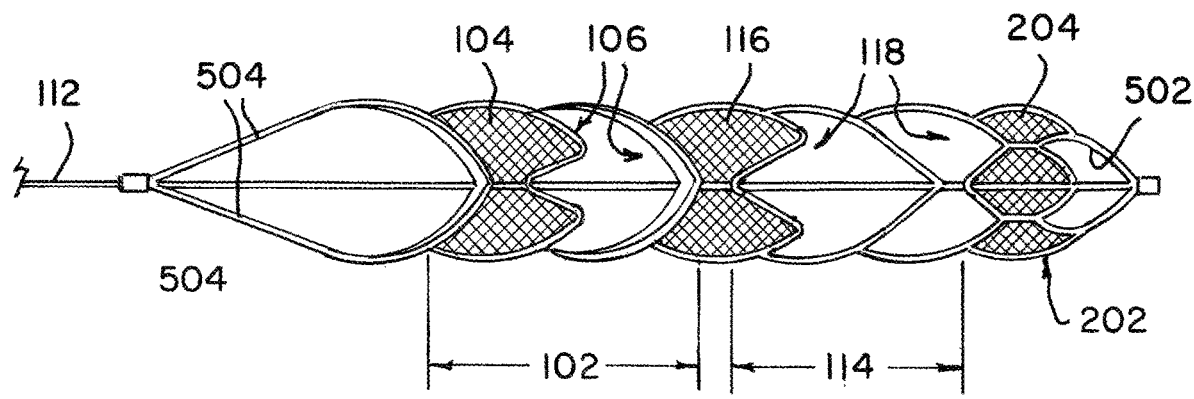
FIG. 7B is a top-view illustration of the exemplary frame for a stentriever depicted in FIG. 7A, according to aspects of the present invention.

FIGS. 7A and 7B are illustrations of an exemplary frame 504 for a stentriever, according to aspects of the present invention. In some examples, the expandable clot engagement sections (i.e., first expandable clot engagement section 102, second expandable clot engagement section 114, distal engagement section 202, etc.) can be attached to a frame 504. The frame 504 can be attached to and extend from the shaft 112, as shown in FIG. 7B, to create the expanded construct described herein. In some examples, a full-length or partial-length inner channel 404 (e.g., the inner channel shown in FIG. 5B) can be provided to extend along the length of the shaft 112 and inside the frame 504. The frame 504 can include any of the features described herein.

In some examples, the distal end of the distal engagement section 202 can, in lieu of distal pores 206 (as shown in FIGS. 1-4), include a distal flow aperture 502. The distal flow aperture 502 can be an area of the distal engagement section 202 that is not covered with distal membrane 204 so as to constrict the flow of aspirate through the distal engagement section 202.

Figure 8:
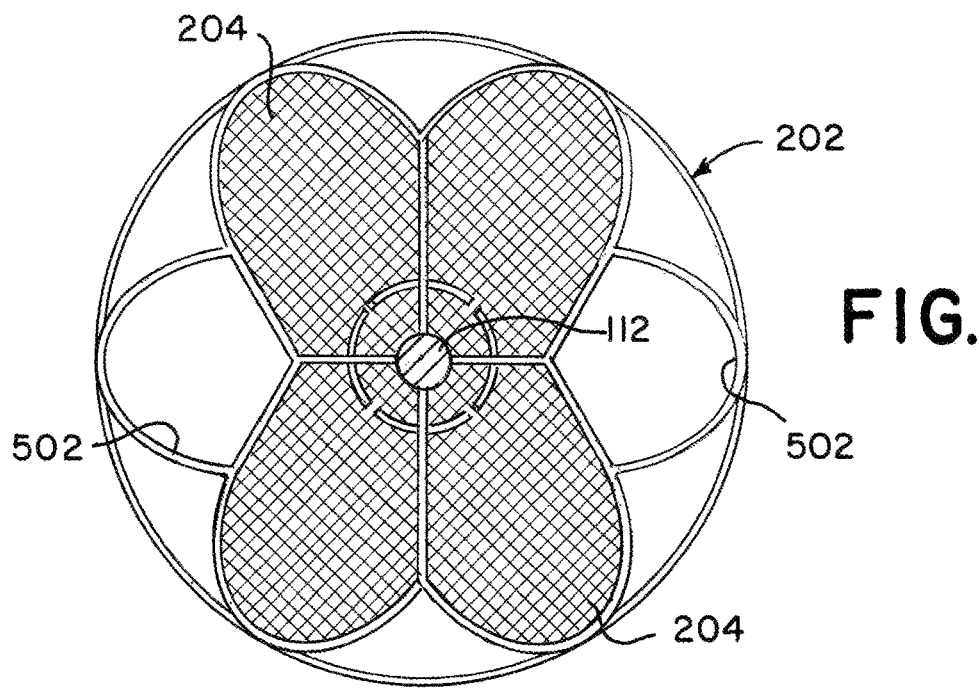
FIG. 8 is an end view of a partially-open distal engagement section, according to aspects of the present invention.

FIG. 8 is an end view of a partially-open distal engagement section 202, according to aspects of the present invention. As described above, the constriction of flow through the distal engagement section 202 can create a negative pressure proximal to the distal engagement section 202, thereby increasing the grip on the clot. The distal flow apertures 502 can be partial openings in the distal membrane 204 that allows a limited amount of fluid flow through the distal membrane 204.

Figure 9A:
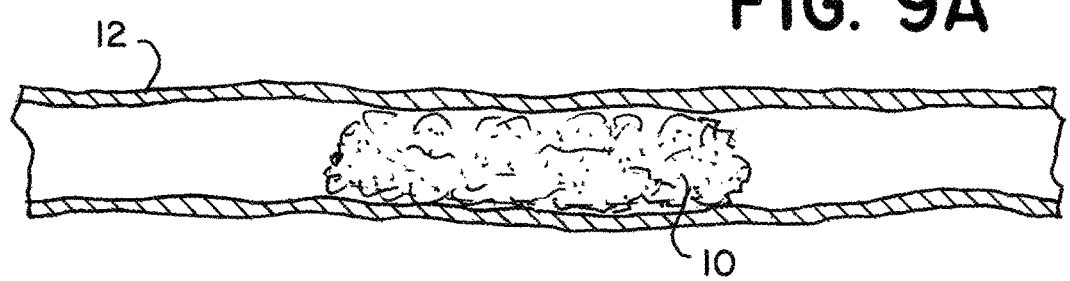
Figure 9B:
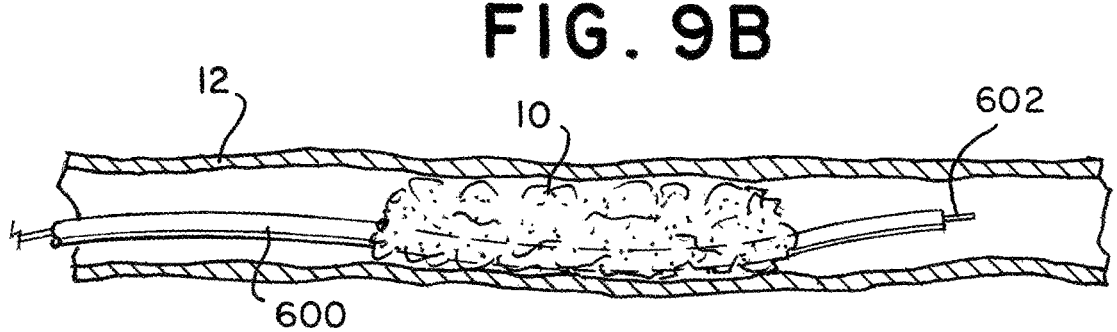

FIGS. 9A-9F depict an exemplary method of deploying a stentriever 100 and removing an occlusive clot 10 from a vessel 12, according to aspects of the present invention. FIG. 9A shows a clot 10 occluding a vessel 12. In FIG. 9B, a guide wire 602 can be fed through the vessel 12 and across the clot 10. A microcatheter 600 can then be advanced over the guide wire 602 and distal to the clot 10. The guide wire 602 can then be removed from within the cannulated microcatheter 600.

Figure 9C:
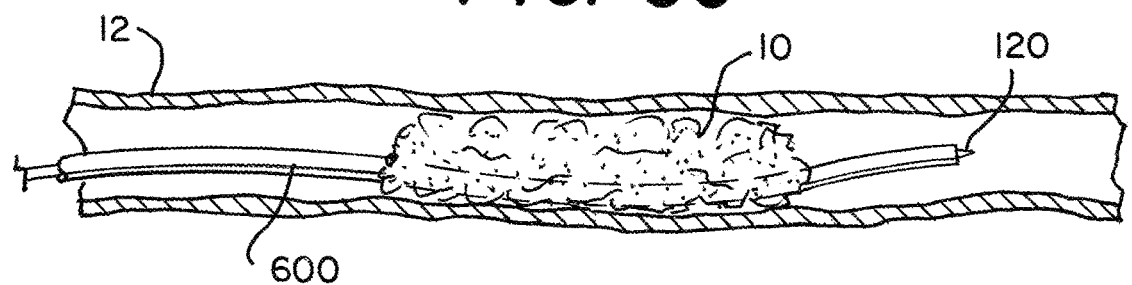

As shown in FIG. 9C, the stentriever 100 can be advanced through the microcatheter 600 in its collapsed configuration until the distal tip 120 of the device reaches the distal end of the microcatheter 600. As shown in FIG. 9D, the microcatheter 600 can then be retracted proximally while the position of the stentriever 100 is maintained. Upon retracting the microcatheter 600, the stentriever 100 can be unsheathed to allow the stentriever 100 to expand into its expanded configuration. In FIG. 9D, only the distal engagement section 202 has been unsheathed.

As shown in FIG. 9E, once the stentriever 100 is unsheathed and fully expanded, an intermediate catheter 300 can be advanced, for example over the microcatheter and/or along the shaft of the stentriever 100, to the proximal flow channel 108. As described above, the proximal flow channel 108 can include a membrane that allows the intermediate catheter to form a seal against the proximal flow channel 108.

As shown in FIGS. 9F and 9G, aspiration can be applied to the intermediate catheter 300. The flow of fluid 16 can be directed by the membrane-covered first expandable clot engagement section 102 (and second expandable clot engagement section 114, as shown in the figure), to pull the clot 10 into the engagement sections. The distal engagement section 202 can include distal pores 206 or distal flow apertures 502, as described herein, to constrict the flow of fluid 16 through the distal engagement section 202. The constricted flow 604 of fluid 16 through the distal engagement section 202 can create a negative pressure area 606 near the expandable clot engagement sections 102,114, which can facilitate pulling the clots into the sections 102,114.

As shown in FIG. 9H, once suction is applied to the proximal flow channel 108 and the clot 10 has been sufficiently captured, the clot 10 can be pulled into the intermediate catheter 300 to be removed from the vessel 12. The position of the intermediate catheter 300 can be maintained, and continued aspiration can be provided to aspirate any clot fragments 14 that may have migrated distal to the stentriever 100, as shown in FIG. 9I. In some examples, the intermediate catheter 300 can be removed along with the stentriever 100 and clot 10 as a single unit through a guide or access catheter.

FIGS. 10A-12B are flow diagrams illustrating methods of removing an occlusive clot with a stentriever. These method steps can be implemented by any of the example means described herein or by similar means, as will be appreciated.

Referring to method 1000 as outlined in FIG. 10A, in step 1010, a stentriever can be delivered into a vessel and across a clot. The stentriever can include a shaft extending between a proximal end and a distal end. An expandable clot engagement section can extend from the shaft. The expandable clot engagement section can include a clot engagement membrane directing a fluid into the engagement section. A clot inlet can be provided in the engagement section for capturing a clot. The stentriever can also include a proximal flow channel with a proximal flow membrane, as described herein. In step 1020, the stentriever can be unsheathed, for example from an access sheath or a microcatheter, to expand the stentriever. Upon expansion of the stentriever, the expandable clot engagement section can engage the clot. In step 1030, an intermediate catheter can be advanced into the vessel and to the proximal flow channel of the stentriever. As described herein, the inner surface of the intermediate catheter can create a seal with the proximal flow membrane. In step 1040, aspiration can be applied to the intermediate catheter such that a flow of fluid is directed by the clot engagement membrane into and into the proximal flow channel to pull the clot into the clot inlet. In step 1050, the stentriever can be pulled proximally to remove the clot from the vessel.

The method 1000 illustrated in FIG. 10A can further include one or more of the steps outlined in FIG. 10B. Referring to method 1060 as outlined in FIG. 10B, in step 1070, the flow of aspiration at the clot engagement section can be constricted by distal pores of a distal engagement section. The constriction of the flow can create a negative pressure near the clot engagement section to pull the clot into the clot inlet. In step 1080, friable-clot fragments can be prevented from passing distal to the stentriever by a plurality of distal clot cells in the distal engagement section and/or the distal pores of the distal engagement section.

The methods 1000 and 1060 as illustrated in FIGS. 10A and 10B can further include one or more of the steps outlined in FIG. 11. Referring to method 1100 as outlined in FIG. 11, in step 1110, a guide wire can be delivered across an occlusive clot. In step 1120, a microcatheter can be advanced along the guide wire and across the clot 10. In step 1130, the guide wire can be removed from the microcatheter, leaving the microcatheter in place within the vessel. In step 1140, a stentriever, as described herein, can be advanced through the microcatheter in a collapsed configuration. In step 1150, the microcatheter can be pulled proximal (i.e., retracted) to allow the stentriever to expand into an expanded configuration, thereby exerting an outward radial force on the clot.

The methods 1000, 1060, and 1100, as illustrated in FIGS. 10A-11 can further include one or more of the steps outlined in FIG. 12A. Referring to method 1200a as outlined in FIG. 12A, in step 1210, the clot can be captured within the stentriever (i.e., within a clot inlet of the stentriever), and the stentriever and the clot can be pulled into the intermediate catheter. In step 1220, the stentriever and captured clot can be removed from the intermediate catheter, leaving the intermediate catheter in place. In step 1230, with the intermediate catheter in place within the vessel, suction can be provided to the intermediate catheter to aspirate any remaining clot fragments in the vessel.

As an alternative to the steps provided in method 1200a as outlined in FIG. 12A, one or more of the steps outlined in FIG. 12B can be performed. Referring to method 1200b, in step 1240, the clot can be captured within the stentriever (i.e., within a clot inlet of the stentriever), and the stentriever and the clot can be pulled into the intermediate catheter. In step 1250, the stentriever, clot, and intermediate catheter can be removed via a guide catheter or an access sheath.

The descriptions contained herein are examples of embodiments of the invention and are not intended in any way to limit the scope of the invention. As described herein, the invention contemplates many variations and modifications of the stentriever device including using alternative geometries of structural elements, combining shapes and structural elements from various example embodiments, using alternative materials, etc. These modifications would be apparent to those having ordinary skill in the art to which this invention relates and are intended to be within the scope of the claims which follow.

The invention claimed is:

1. A stentriever for removing a clot from a vessel, comprising:
   a shaft extending between a proximal end and a distal end;
   a first expandable clot engagement section directly connected to and extending from the shaft and comprising a first clot engagement membrane directing an aspiration into the first expandable clot engagement section;
   a second expandable clot engagement section extending from the shaft and positioned distal to the first expandable clot engagement section;
   an intermediate flow channel positioned proximal to and adjacent the second expandable clot engagement section;
   a proximal flow channel positioned proximal to and adjacent the first expandable clot engagement section, the proximal flow channel comprising a proximal flow membrane directing the aspiration from the first expandable clot engagement section and to the proximal flow channel; and
   a distal engagement section positioned distal to the first expandable clot engagement section and extending from the shaft,
   wherein the stentriever comprises a collapsed configuration to be inserted into a microcatheter,
   wherein the stentriever comprises an expanded configuration for exerting an outward radial force on the clot, and
   wherein, when the stentriever is in the expanded configuration, the first expandable clot engagement section has a larger diameter than the proximal flow channel, causing the aspiration to be directed from the first expandable clot engagement section by the first clot engagement membrane and into the proximal flow channel.

2. The stentriever of claim 1, wherein the first expandable clot engagement section further comprises a first clot inlet capturing the clot.

3. The stentriever of claim 1, wherein the proximal flow channel comprises:
   a collapsed configuration to be inserted into the microcatheter, and
   an expanded configuration wherein the proximal flow channel exerts a radial force on an intermediate catheter,
   wherein, in the expanded configuration, the proximal flow membrane engages with an inner surface of the intermediate catheter at a proximal seal area to direct aspiration flow.

4. The stentriever of claim 1, wherein the second expandable clot engagement section comprises a second clot engagement membrane directing the aspiration into the second expandable clot engagement section.

5. The stentriever of claim 1, wherein the distal engagement section comprises a plurality of distal clot cells capturing clot fragments.

6. The stentriever of claim 5, wherein the distal engagement section comprises a distal membrane, and wherein the distal membrane comprises distal pores constricting flow of the aspiration into the distal engagement section.

7. The stentriever of claim 6, wherein:
   the first expandable clot engagement section further comprises a first clot inlet capturing the clot, and
   the distal membrane constricts flow from the distal engagement section to the proximal flow channel to create a negative pressure at the first expandable clot engagement section, thereby pulling the clot into the first clot inlet.

8. A system for removing a clot from a vessel, the system comprising:
   a stentriever comprising:
      a shaft extending between a proximal end and a distal end;
      a first expandable clot engagement section directly connected to and extending from the shaft and comprising a first clot engagement membrane directing an aspiration into the first expandable clot engagement section;
      a second expandable clot engagement section extending from the shaft and positioned distal to the first expandable clot engagement section;
      an intermediate flow channel positioned proximal to and adjacent the second expandable clot engagement section;
      a proximal flow channel positioned proximal to and adjacent the first expandable clot engagement section, the proximal flow channel comprising a proximal flow membrane; and
      a distal engagement section positioned distal to the first expandable clot engagement section and extending from the shaft; and
   an intermediate catheter,
   wherein the stentriever comprises a collapsed configuration to be inserted into a microcatheter,
   wherein the stentriever comprises an expanded configuration to be expanded in the vessel,
   wherein, in the expanded configuration, the proximal flow channel exerts a radial force on the intermediate catheter,
   wherein the proximal flow membrane seals against an inner surface of the intermediate catheter, and
   wherein, when the stentriever is in the expanded configuration, the first expandable clot engagement section has a larger diameter than the proximal flow channel, causing the aspiration to be directed from the first expandable clot engagement section by the first clot engagement membrane and into the proximal flow channel.

9. The system of claim 8, wherein the first expandable clot engagement section further comprises a first clot inlet capturing the clot.

10. The system of claim 8, wherein the second expandable clot engagement section comprises a second clot engagement membrane directing an aspiration into the second expandable clot engagement section.

11. The system of claim 8, wherein the distal engagement section comprises a plurality of distal pores constricting flow of the aspiration into the distal engagement section.

12. A stentriever for removing a clot from a vessel, comprising:
   a shaft extending between a proximal end and a distal end;
   a first expandable clot engagement section directly connected to and extending from the shaft and comprising a first clot engagement membrane directing an aspiration into the first expandable clot engagement section;

a second expandable clot engagement section extending from the shaft, the second expandable clot engagement section being positioned distal to the first expandable clot engagement section, the second expandable clot engagement section comprising a second clot engagement membrane directing the aspiration into the second expandable clot engagement section;

a distal engagement section positioned distal to the first expandable clot engagement section and the second expandable clot engagement section and extending from the shaft; and an inner channel extending from a position proximal to and adjacent the first expandable clot engagement section to a position proximate the distal engagement section, the inner channel comprising:
- a first inner channel membrane positioned along a length of the inner channel proximal to and adjacent the first expandable clot engagement section; and
- a second inner channel membrane positioned along the length of the inner channel proximal to and adjacent the second expandable clot engagement section, the second inner channel membrane being separated from the first inner channel membrane along a length of the inner channel, wherein the stentriever comprises a collapsed configuration to be inserted into a microcatheter, wherein the stentriever comprises an expanded configuration for exerting an outward radial force on the clot, and wherein, when the stentriever is in the expanded configuration, the first expandable clot engagement section has a larger diameter than the inner channel, causing the aspiration to be directed from the first expandable clot engagement section by the first clot engagement membrane and into the first inner channel membrane.

13. The stentriever of claim 12, wherein the distal engagement section comprises a plurality of distal clot cells capturing clot fragments.

14. The stentriever of claim 13, wherein the distal engagement section comprises a distal membrane, and wherein the distal membrane comprises distal pores constricting flow of the aspiration into the distal engagement section.

* * * * *